(12) United States Patent
Bernard et al.

(10) Patent No.: US 10,392,623 B2
(45) Date of Patent: Aug. 27, 2019

(54) L-ARABINOSE ASSIMILATION PATHWAY AND USES THEREOF

(71) Applicant: DEINOVE, Grabels (FR)

(72) Inventors: Remi Bernard, Castelnau le Lez (FR); Assia Zigha, Montpellier (FR); Pascale Joseph, Montpellier (FR); Jean-Paul Leonetti, Castelnau le Lez (FR)

(73) Assignee: DEINOVE, Grabels (FR)

( * ) Notice: Subject to any disclaimer, the term of this patent is extended or adjusted under 35 U.S.C. 154(b) by 0 days.

(21) Appl. No.: 15/548,424

(22) PCT Filed: Feb. 15, 2016

(86) PCT No.: PCT/EP2016/053201
§ 371 (c)(1),
(2) Date: Aug. 3, 2017

(87) PCT Pub. No.: WO2016/131788
PCT Pub. Date: Aug. 25, 2016

(65) Prior Publication Data
US 2018/0016586 A1  Jan. 18, 2018

(30) Foreign Application Priority Data
Feb. 16, 2015  (EP) .................................... 15305232

(51) Int. Cl.
| | |
|---|---|
| C12P 7/06 | (2006.01) |
| C12N 15/74 | (2006.01) |
| C12N 9/12 | (2006.01) |
| C12N 9/90 | (2006.01) |
| C12N 15/52 | (2006.01) |
| C12P 7/04 | (2006.01) |

(52) U.S. Cl.
CPC ........... *C12N 15/74* (2013.01); *C12N 9/1205* (2013.01); *C12N 9/90* (2013.01); *C12N 15/52* (2013.01); *C12P 7/04* (2013.01); *C12P 7/065* (2013.01); *C12Y 207/01016* (2013.01); *C12Y 501/03004* (2013.01); *C12Y 503/01004* (2013.01); *Y02E 50/17* (2013.01)

(58) Field of Classification Search
CPC .... C12Y 501/03004; C12Y 503/01004; C12N 9/90
USPC ....................................................... 435/161
See application file for complete search history.

(56) References Cited

U.S. PATENT DOCUMENTS

| | | |
|---|---|---|
| 9,034,619 B2 | 5/2015 | Biton et al. |
| 9,181,564 B2 | 11/2015 | Leonetti et al. |
| 9,725,741 B2 | 8/2017 | Biton et al. |

FOREIGN PATENT DOCUMENTS

| | | |
|---|---|---|
| WO | WO 03/095627 | 11/2003 |
| WO | WO 2009/011591 | 1/2009 |
| WO | WO 2009/063079 | 5/2009 |
| WO | WO 2010/130806 | 11/2010 |

OTHER PUBLICATIONS

Becker, J. et al. "A Modified *Saccharomyces cerevisiae* Strain That Consumes $_L$-Arabinose and Produces Ethanol" *Applied and Environmental Microbiology*, Jul. 1, 2003, pp. 4144-4150, vol. 69, No. 7.
Deanda, K. et al. "Development of an Arabinose-Fermenting *Zymomonas mobilis* Strain by Metabolic Pathway Engineering" *Applied and Environmental Microbiology*, Dec. 1, 1996, pp. 4465-4470, vol. 62, No. 12.
Kawaguchi, H. et al. "Engineering of an $_L$-arabinose metabolic pathway in *Corynebacterium glutamicum*" *Applied Microbiology Biotechnology*, 2008, pp. 1053-1062, vol. 77, No. 5.
Anonymous, "Deinove teams up with MBI, pioneer of AFEX technology, to evaluate its process on industrial biomass" Oct. 15, 2014, retrieved from the Internet on Jun. 6, 2015, URL:http://www.globenewswire.com/news-relese/2014/10/15/673503/10102808/en/DEINOVE-teams-up-with-MBI-pioneer-of-AFEX-technology-to-evaluate-its-process-on-industrial-biomass.html, pp. 1-5.
Anonymous, "Deinol—An Innovative and Competitive Solution to Create Value in the 2G-Ethanol Industry" Oct. 1, 2014, retrieved from the Internet on Jun. 16, 2015, URL:http://www.deinove.com/sites/default/files/pdf_news/deinol_testing_campaign_141015.pdf, pp. 1-15.
Written Opinion in International Application No. PCT/EP2016/053201, dated May 2, 2016, pp. 1-6.

*Primary Examiner* — Tekchand Saidha
(74) *Attorney, Agent, or Firm* — Saliwanchik, Lloyd & Eisenschenk

(57) ABSTRACT

The present invention relates to a new L-arabinose assimilation pathway and uses thereof. In particular, the present invention relates to polypeptides exhibiting L-arabinose isomerase, L-ribulokinase or L-ribulose-5-phosphate-4-epimerase activity, and recombinant host cells expressing said polypeptides. The present invention also relates to a method of producing a fermentation product, preferably ethanol, from an arabinose containing substrate, using a polypeptide or a host cell of the invention.

19 Claims, 5 Drawing Sheets
Specification includes a Sequence Listing.

L-ARABINOSE ASSIMILATION PATHWAY AND USES THEREOF

CROSS-REFERENCE TO RELATED APPLICATION

This application is the U.S. national stage application of International Patent Application No. PCT/EP2016/053201, filed Feb. 15, 2016.

The Sequence Listing for this application is labeled "Seq-List.txt" which was created on Feb. 9, 2016 and is 17 KB. The entire content of the sequence listing is incorporated herein by reference in its entirety.

FIELD OF THE INVENTION

The present invention relates to a novel L-arabinose metabolic pathway and uses thereof, in particular in biomass conversion technologies to produce biofuels or other compounds of interest.

BACKGROUND OF THE INVENTION

Biorefinery offers the potential to use a wide variety of non-food biomass resources such as agricultural residues, forestry and municipal wastes or dedicated crops such as switchgrass or miscanthus, to produce valuable biochemicals, biomaterials and biofuels.

These compounds may be produced from these vegetal biomass materials through a number of process steps, including biomass degradation and fermentation, using e.g., chemical, physical and/or biological treatments and catalysts. Typically, biorefinery requires pretreatment of the biomass to at least partially hydrolyze the hemicellulose, remove the lignin and de-crystallize the cellulose, so that cellulase enzymes can access their substrate.

*Deinococcus* bacteria are gram positive bacteria that were firstly isolated in 1956 by Anderson and collaborators. These extremophile organisms are resistant to DNA damage by UV and ionizing radiations or by cross-linking agent (mitomycin C) and are tolerant to desiccation. WO 01/023526 shows the unusual resistance of *Deinococcus* to radiation and further proposes their engineering and use in bioremediation. WO 2009/063079 shows that *Deinococcus* bacteria can resist to solvents and transform biomass to generate ethanol. WO 2010/130806 further discloses recombinant *Deinococcus* strains wherein ethanol biosynthesis genes have been inserted. These recombinant strains do exhibit improved performance in the production of ethanol. WO 2013/092965 also discloses a further generation of improved *Deinococcus* bacteria, with higher and remarkable biomass degradation and biofuel production properties.

Because the feedstock represents a significant portion of all costs, and in order to obtain high yields of production, an efficient process requires using microorganism strains that have the capacity to metabolize all major sugars found in vegetal biomasses such as glucose, xylose, arabinose, galactose and/or mannose. In particular, cellulosic biomass can comprise 3 to 15% L-arabinose component and improvement in the assimilation of this pentose may significantly decrease the costs of the whole process and increase production yields.

As currently known *Deinococcus* bacteria are not able to produce ethanol from L-arabinose, there is a need for new L-arabinose metabolic pathway that can be used to produce recombinant *Deinococcus* bacteria exhibiting efficient conversion of L-arabinose to ethanol or to any other fermentation product or compound of industrial interest.

SUMMARY OF THE INVENTION

The inventors herein identified a novel functional L-arabinose assimilation operon from *Deinococcus roseus* that confers the ability to utilize L-arabinose as sole carbon source.

Accordingly, in a first aspect, the present invention relates to a recombinant host cell comprising a nucleic acid construct, expression cassette or vector comprising (i) a nucleic acid sequence encoding a polypeptide comprising an amino acid sequence having at least 72% identity to SEQ ID NO: 1 and exhibiting L-arabinose isomerase activity, or a functional fragment thereof, (ii) a nucleic acid sequence encoding a polypeptide comprising an amino acid sequence having at least 73% identity to SEQ ID NO: 3 and exhibiting L-ribulokinase activity, or a functional fragment thereof; and/or (iii) a nucleic acid sequence encoding a polypeptide comprising an amino acid sequence having at least 73% identity to SEQ ID NO: 5 and exhibiting L-ribulose-5-phosphate 4 epimerase activity, or a functional fragment thereof.

The recombinant nucleic acid construct, expression cassette or vector may comprise a nucleic acid sequence encoding a polypeptide comprising an amino acid sequence having at least 75, 80, 90, 95, 98, 99% identity to SEQ ID NO: 1 and exhibiting L-arabinose isomerase activity, or a functional fragment thereof. Preferably, the nucleic acid sequence encodes a polypeptide comprising, or consisting of, the amino acid sequence of SEQ ID NO: 1.

The recombinant nucleic acid construct, expression cassette or vector may comprise a nucleic acid sequence encoding a polypeptide comprising an amino acid sequence having at least 75, 80, 90, 95, 98, 99% identity to SEQ ID NO: 3 and exhibiting L-ribulokinase activity, or a functional fragment thereof. Preferably, the nucleic acid sequence encodes a polypeptide comprising, or consisting of, the amino acid sequence of SEQ ID NO: 3.

The recombinant nucleic acid construct, expression cassette or vector may comprise a nucleic acid sequence encoding a polypeptide comprising an amino acid sequence having at least 75, 80, 90, 95, 98, 99% identity to SEQ ID NO: 5 and exhibiting L-ribulose-5-phosphate 4 epimerase activity, or a functional fragment thereof. Preferably, the nucleic acid sequence encodes a polypeptide comprising, or consisting of, the amino acid sequence of SEQ ID NO: 5.

The recombinant nucleic acid construct, expression cassette or vector may comprise a nucleic acid sequence encoding a polypeptide comprising, or consisting of, the amino acid sequence of SEQ ID NO: 1, a nucleic acid sequence encoding a polypeptide comprising, or consisting of, the amino acid sequence of SEQ ID NO: 3 and a nucleic acid sequence encoding a polypeptide comprising, or consisting of, the amino acid sequence of SEQ ID NO: 5.

Preferably, the host cell is a *Deinococcus* bacterium, more preferably a *Deinococcus* bacterium producing ethanol or producing an isoprenoid compound. Preferably, the bacterium is selected from the group consisting of *D. geothermalis, D. aquatilis, D. gobiensis, D. cellulolysiticus, D. deserti, D. murrayi, D. maricopensis* and *D. radiodurans*, more preferably from the group consisting of *D. geothermalis, D. cellulolysiticus, D. deserti, D. murrayi, D. maricopensis* and *D. radiodurans*, and even more preferably is *D. geothermalis*.

The present invention also relates to a cell extract of the recombinant cell of the invention.

In a second aspect, the present invention relates to an isolated or purified polypeptide comprising, or consisting of, (i) an amino acid sequence having at least 72% identity to SEQ ID NO: 1 and exhibiting L-arabinose isomerase activity, or a functional fragment thereof, (ii) an amino acid sequence having at least 71% identity to SEQ ID NO: 3 and exhibiting L-ribulokinase activity, or a functional fragment thereof, or (iii) an amino acid sequence having at least 72% identity to SEQ ID NO: 5 and exhibiting L-ribulase-5-phosphate 4 epimerase activity, or a functional fragment thereof. The present invention also relates to a recombinant nucleic acid construct, expression cassette or vector, or host cell comprising a nucleic acid sequence encoding such polypeptide. In particular, the present invention relates to a recombinant host cell comprising a recombinant nucleic acid construct, expression cassette or vector of the invention.

In another aspect, the present invention relates to a recombinant *Deinococcus* bacterium or related bacterium comprising a heterologous nucleic acid sequence encoding a polypeptide exhibiting L-arabinose isomerase activity, a polypeptide exhibiting L-ribulokinase activity, and/or a polypeptide exhibiting L-ribulose-5-phosphate 4 epimerase activity. Preferably, said bacterium comprises one or several nucleic acid constructs, expression cassettes and/or expression vectors encoding one or several polypeptides of the invention. Preferably, the bacterium is a *Deinococcus* bacterium selected from the group consisting of *D. geothermalis, D. cellulolysiticus, D. deserti, D. aquatilis, D. gobiensis, D. murrayi, D. maricopensis* and *D. radiodurans*, more preferably from the group consisting of *D. geothermalis, D. cellulolysiticus, D. deserti, D. murrayi, D. maricopensis* and *D. radiodurans*, and even more preferably is *D. geothermalis*.

In a further aspect, the present invention relates to a method of producing a polypeptide of the invention, comprising (a) culturing a host cell of the invention expressing said polypeptide; and (b) recovering said polypeptide from the cell culture; and (c) optionally, purifying said polypeptide.

The present invention also relates to a method of producing a fermentation product comprising contacting an arabinose containing substrate, preferably an arabinose containing cellulosic biomass, with a polypeptide of the invention or a host cell of the invention expressing said polypeptide, and optionally recovering the fermentation product.

The fermentation product may be biofuel, such as ethanol, butanol, propanol, glycerol methanol, isopropanol, propanediol, glycerol or 2-3 butanediol, an organic acid such as formate, acetate, lactate, butyrate, gluconate, xylonate, citrate, succinate, propionate, fumarate, malate, pyruvate, itaconic acid and kojic acid, and their salts or esters, an isoprenoid compound, or a pharmaceutical compound such as antibiotics, bacteriostatic compounds, anti-metabolite, chemotherapeutic compounds, anti-parasitic agents, antifungal agents, anti-viral compounds, cytokine-activity compounds or cell-growth factors. Preferably, the fermentation product is ethanol or an isoprenoid compound.

DETAILED DESCRIPTION OF THE INVENTION

Figure 1:
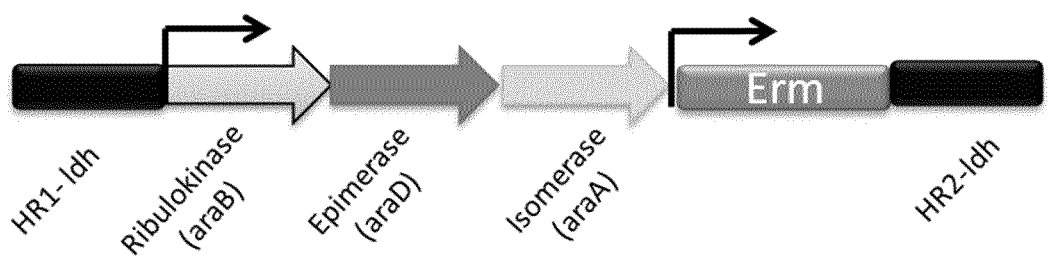
FIG. 1: Expression cassette comprising the *D. roseus* arabinose operon to be inserted at the ldh locus in *D. geothermalis*.

The bacterial L-arabinose metabolic pathway is co-factor independent and consists of L-arabinose isomerase (AraA) converting L-arabinose to L-ribulose, L-ribulokinase (AraB) converting L-ribulose to L-ribulose-5-phosphase, and L-ribulose-5-phosphate-4-epimerase (AraD) converting L-ribulose-5-phosphase to D-xylulose-5-phosphate which subsequently enters the Pentose Phosphate Pathway (PPP).

The inventors herein identified a novel functional L-arabinose pathway operon from *Deinococcus roseus* and showed that the introduction and expression of this operon in an ethanologenic *Deinococcus geothermalis* strain confers the ability to utilize L-arabinose as sole carbon source while producing ethanol. They also showed that the expression of this operon in a *Deinococcus* bacterium having a geraniol synthase confers the ability to produce the monoterpene geraniol by utilizing L-arabinose as sole carbon source. They further demonstrated that, surprisingly, thanks to this operon, the recombinant *Deinococcus* strain can efficiently co-assimilate L-arabinose and glucose and/or xylose without any diauxie and is thus a promising biocatalyst to increase the production yield of fermentation processes in which mixed pentose and hexose sugars are co-fermented.

The identified L-arabinose pathway operon encodes three new enzymes: the L-arabinose isomerase (AraA, EC 5.3.1.4) of SEQ ID NO:1 comprising 500 amino acid residues, the L-ribulokinase (AraB, EC 2.7.1.16) of SEQ ID NO:3 comprising 563 amino acid residues, and the L-ribulose-5-phosphate-4-epimerase (AraD, EC 5.1.3.4) of SEQ ID NO:5 comprising 217 amino acid residues.

Definitions

As used herein, the terms "peptide", "oligopeptide", "polypeptide" and "protein" are employed interchangeably and refer to a chain of amino acids linked by peptide bonds, regardless of the number of amino acids forming said chain.

As used herein, the term "sequence identity" or "identity" refers to the number (%) of matches (identical amino acid residues) in positions from an alignment of two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithms (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as http://blast.ncbi.nlm.nih.gov/ or (see Worldwide Website: ebi.ac.uk/Tools/emboss/)). Those skilled in the art can determine appropriate parameters for measuring alignment, including any algorithms needed to achieve maximal alignment over the full length of the sequences being compared. Preferably, for purposes herein, % amino acid sequence identity values refers to values generated using the pair wise sequence alignment program EMBOSS Needle that creates an optimal global alignment of two sequences using the Needleman-Wunsch algorithm, wherein all search parameters are set to default values, i.e. Scoring matrix =BLOSUM62, , Gap open =10, , Gap extend =0.5, , End gap penalty =false, End gap open =10 and End gap extend =0.5.

As used herein, the term "functional fragment" refers to a fragment of a polypeptide of the invention, comprising at least 100, 150, 200, 250, 300, 350, 400, 450 or 500 contiguous amino acids of said polypeptide, and retaining the enzymatic activity of the entire polypeptide. Preferably, the functional fragment retains substrate specificity and/or substrate affinity and/or optimal pH and/or optimal temperature of the entire polypeptide. These properties can be easily assessed by the skilled person using well known methods.

As used herein, the term "purified" or "isolated", in relation to a polypeptide or nucleic acid, refers to a polypeptide or nucleic acid which is not in its natural medium or form. The term "isolated" thus includes a polypeptide or nucleic acid removed from its original environment, e.g., the natural environment if it is naturally occurring. For instance, an isolated polypeptide is typically devoid of at least some proteins or other constituents of the cells to which it is normally associated or with which it is normally admixed or in solution. An isolated polypeptide includes said polypeptide naturally-produced contained in a cell lysate; the polypeptide in a purified or partially purified form, the recombinant polypeptide, the polypeptide which is expressed or secreted by a cell, as well as the polypeptide in a heterologous host cell or culture. In relation to a nucleic acid, the term isolated or purified indicates e.g., that the nucleic acid is not in its natural genomic context (e.g., in a vector, as an expression cassette, linked to a promoter, or artificially introduced in a heterologous host cell).

As used herein the term "heterologous" with reference to a polynucleotide or polypeptide refers to a polynucleotide or polypeptide that does not naturally occur in a host cell. In some preferred embodiments, this term refers to a polynucleotide or polypeptide that does not naturally occur in the *Deinococcus* host cell but is obtained from another *Deinococcus* strain.

As used herein the term "endogenous" with reference to a polynucleotide or polypeptide refers to a polynucleotide or polypeptide that naturally occurs in a host cell.

As used herein, the term "arabinose" may refer to D-arabinose or L-arabinose, preferably L-arabinose.

In a first aspect, the present invention relates to a polypeptide comprising an amino acid sequence having at least 72% identity to SEQ ID NO: 1 and exhibiting L-arabinose isomerase activity, or a functional fragment thereof, an amino acid sequence having at least 73% identity to SEQ ID NO: 3 and exhibiting L-ribulokinase activity, or a functional fragment thereof, or an amino acid sequence having at least 73% identity to SEQ ID NO: 5 and exhibiting L-ribulose-5-phosphate 4 epimerase activity, or a functional fragment thereof.

In a first embodiment, the polypeptide comprises an amino acid sequence having at least 72% identity to SEQ ID NO: 1 and exhibiting L-arabinose isomerase activity, or a functional fragment thereof.

The terms "L-arabinose isomerase" and "AraA" are used herein interchangeably and refer to an enzyme converting L-arabinose to L-ribulose. In particular, these terms refers to an enzyme having an activity described as EC 5.3.1.4 according to the International Union of Biochemistry and Molecular Biology enzyme nomenclature. The L-arabinose isomerase activity may be assessed using any method known by the skilled person. For example, the L-arabinose isomerase activity may be assayed using L-arabinose as substrate and detecting production of L-ribulose with the cysteine-carbazole test as described in the article of Dische and Borenfreund (J Biol Chem. 1951 October; 192(2):583-7) or Englesberg (J Bacteriol. 1961 June; 81:996-1006).

Preferably, the polypeptide comprises, or consists of, an amino acid sequence having at least 73, 74, 75, 76, 77, 78, 79, 80, 81, 82, 83, 84, 85, 86, 87, 88, 89, 90, 91, 92, 93, 94, 95, 96, 97, 98 or 99% identity to SEQ ID NO: 1. Preferably, the percentage of identity is determined over more than 10% of length of SEQ ID NO: 1, more preferably over more than 20, 30, 40, 50, 60, 70, 80, 90, 95, 99 or 100% of length of SEQ ID NO: 1. In a particular embodiment, the polypeptide comprises, or consists of, the amino acid sequence of SEQ ID NO: 1.

Alternatively, the polypeptide may comprise, or consist of, a sequence that differs from the sequence set forth in SEQ ID NO: 1 by 1, 2, 3, 4, 5, 6, 7, 8, 9, 10, 11, 12, 13, 14, 15, 16, 17, 18, 19 or 20 substitutions, insertions and/or deletions of amino acid residues, preferably by 1, 2, 3, 4, 5, 6, 7, 8, 9, 10, 11, 12, 13, 14 or 15 substitutions, insertions and/or deletions of amino acid residues.

The polypeptide may also be a functional fragment of an amino acid sequence having at least 72% identity to SEQ ID NO: 1 and exhibiting L-arabinose isomerase activity. Preferably, the functional fragment comprises, or consists of, at least 100, 150, 200, 250, 300, 350, 400, 450 or 500 contiguous amino acids of an amino acid sequence having at least 72% identity to SEQ ID NO: 1, preferably of the amino acid sequence SEQ ID NO: 1.

In a second embodiment, the polypeptide comprises an amino acid sequence having at least 73% identity to SEQ ID NO: 3 and exhibiting L-ribulokinase activity, or a functional fragment thereof.

The terms "ribulokinase", "L-ribulokinase" and "AraB" are used herein interchangeably and refer to an enzyme converting L-ribulose to L-ribulose-5-phosphase. In particular, these terms refers to an enzyme having an activity described as EC 2.7.1.16 according to the International Union of Biochemistry and Molecular Biology enzyme nomenclature. The ribulokinase activity may be assessed using any method known by the skilled person. For example, the ribulokinase activity may be assayed by modified cysteine-carbazole reaction as described in the article of Tokgöz et al (Turk J Biol, 2014, 38: 633-639) or by measuring the production of $^{14}C$-labeled ribulose phosphate as described in the article of Schleif et al. (J. Bacteriol, 1973 July; 115(1): 9-14).

Preferably, the polypeptide comprises, or consists of, an amino acid sequence having at least 74, 75, 76, 77, 78, 79, 80, 81, 82, 83, 84, 85, 86, 87, 88, 89, 90, 91, 92, 93, 94, 95, 96, 97, 98 or 99% identity to SEQ ID NO: 3. Preferably, the percentage of identity is determined over more than 10% of length of SEQ ID NO: 3, more preferably over more than 20, 30, 40, 50, 60, 70, 80, 90, 95, 99 or 100% of length of SEQ ID NO: 3. In a particular embodiment, the polypeptide comprises, or consists of, the amino acid sequence of SEQ ID NO: 3.

Alternatively, the polypeptide may comprise, or consist of, a sequence that differs from the sequence set forth in SEQ ID NO: 3 by 1, 2, 3, 4, 5, 6, 7, 8, 9, 10, 11, 12, 13, 14, 15, 16, 17, 18, 19 or 20 substitutions, insertions and/or deletions of amino acid residues, preferably by 1, 2, 3, 4, 5, 6, 7, 8, 9, 10, 11, 12, 13, 14 or 15 substitutions, insertions and/or deletions of amino acid residues.

The polypeptide may also be a functional fragment of an amino acid sequence having at least 73% identity to SEQ ID NO: 3 and exhibiting L-ribulokinase activity. Preferably, the functional fragment comprises, or consists of, at least 100, 150, 200, 250, 300, 350, 400, 450 or 500 contiguous amino acids of an amino acid sequence having at least 73% identity to SEQ ID NO: 3, preferably of the amino acid sequence of SEQ ID NO: 3.

In a third embodiment, the polypeptide comprises an amino acid sequence having at least 73% identity to SEQ ID NO: 5 and exhibiting L-ribulose-5-phosphate 4 epimerase activity, or a functional fragment thereof.

The terms "L-ribulose-5-phosphate 4 epimerase", "L-ru5P", "phosphoribulose isomerase", "ribulose phosphate 4-epimerase" and "AraD" are used herein interchangeably and refer to an enzyme converting L-ribulose-5-phosphase to D-xylose-5-phosphate. In particular, these terms refers to an enzyme having an activity described as EC 5.1.3.4 according to the International Union of Biochemistry and Molecular Biology enzyme nomenclature. The L-ribulose-5-phosphate 4 epimerase activity may be assessed using any method known by the skilled person. For example, this activity may be assayed using L-ribulose 5-phosphate as substrate and measuring the production of D-xylulose-5-phosphate as described in the article of Davis et al. (J. Biol. Chem. 1972, 247:5862-5866).

Preferably, the polypeptide comprises, or consists of, an amino acid sequence having at least 74, 75, 76, 77, 78, 79, 80, 81, 82, 83, 84, 85, 86, 87, 88, 89, 90, 91, 92, 93, 94, 95, 96, 97, 98 or 99% identity to SEQ ID NO: 5. Preferably, the percentage of identity is determined over more than 10% of length of SEQ ID NO: 5, more preferably over more than 20, 30, 40, 50, 60, 70, 80, 90, 95, 99 or 100% of length of SEQ ID NO: 5. In a particular embodiment, the polypeptide comprises, or consists of, the amino acid sequence of SEQ ID NO: 5.

Alternatively, the polypeptide may comprise, or consist of, a sequence that differs from the sequence set forth in SEQ ID NO: 5 by 1, 2, 3, 4, 5, 6, 7, 8, 9, 10, 11, 12, 13, 14, 15, 16, 17, 18, 19 or 20 substitutions, insertions and/or deletions of amino acid residues, preferably by 1, 2, 3, 4, 5, 6, 7, 8, 9, 10, 11, 12, 13, 14 or 15 substitutions, insertions and/or deletions of amino acid residues.

The polypeptide may also be a functional fragment of an amino acid sequence having at least 73% identity to SEQ ID NO: 5 and exhibiting L-ribulose-5-phosphate 4 epimerase activity. Preferably, the functional fragment comprises, or consists of, at least 100, 150, 200, 250, 300, 350, 400, 450 or 500 contiguous amino acids of an amino acid sequence having at least 73% identity to SEQ ID NO: 5, preferably of the amino acid sequence of SEQ ID NO: 5.

The polypeptides of the invention may also be hybrid polypeptides or fusion polypeptides in which a polypeptide as described above is fused at its N-terminus and/or C-terminus to another polypeptide. Techniques for producing fusion polypeptides are well known in the art, and include ligating the coding sequences encoding the polypeptide and the addition region of another polypeptide so that they are in frame and that expression of the fusion polypeptide is under control of the same promoter(s) and terminator. The addition region of the fusion polypeptide can be selected in order to enhance the stability of the enzyme, to promote the secretion (such as a N-terminal hydrophobic signal peptide) of the fusion protein from a cell (such as a bacterial cell or a yeast cell), or to assist in the purification of the fusion protein. More particularly, the additional region can be a tag useful for purification or immobilization of the enzyme. Such a tag is well-known by the person skilled in the art, for instance a His tag ($His_6$), a FLAG tag, a HA tag (epitope derived from the Influenza protein haemagglutinin), a maltose-binding protein (MPB), a MYC tag (epitope derived from the human proto-oncoprotein MYC) or a GST tag (small glutathione-S-transferase). A fusion polypeptide can further comprise a cleavage site for proteases or chemical agents, between the enzyme and the addition region. Upon secretion of the fusion protein, the site is cleaved releasing the two separate polypeptides.

The polypeptides of the invention may also be fused at their N-terminus and/or C-terminus to one or several polypeptides exhibiting distinct enzymatic activity.

Polypeptides of the invention may be produced by recombinant techniques, or, when naturally-occurring, they may be isolated or purified from natural sources. They may be expressed, derived, secreted, isolated, or purified from a host cell, e.g. a *Deinococcus* bacterium. The polypeptides are preferably in isolated or purified form. They may be purified by techniques known per se in the art, and stored under conventional techniques.

Polypeptides of the invention may be naturally-occurring, recombinant and/or synthetic and, optionally may be modified (e.g., chemically, enzymatically, physically, etc.). In particular, they may be modified to improve e.g., their stability or activity.

The polypeptides may be in soluble form, or on solid phase. In particular, they may be bound to cell membranes or lipid vesicles, or to synthetic supports such as glass, plastic, polymers, filter, membranes, e.g., in the form of beads, columns, plates and the like.

The present invention further relates to a nucleic acid encoding a polypeptide of the invention as described above.

Preferably, the nucleic acid is a recombinant, isolated or purified nucleic acid. As used herein, the term "recombinant nucleic acid" designates a nucleic acid which has been engineered and is not found as such in wild type bacteria.

The nucleic acid can be DNA (cDNA or gDNA), RNA, or a mixture of the two. It can be in single stranded form or in duplex form or a mixture of the two. It can comprise modified nucleotides, comprising for example a modified bond, a modified purine or pyrimidine base, or a modified sugar. It can be prepared by any method known to one skilled in the art, including chemical synthesis, recombination, and mutagenesis. The nucleic acid according to the invention may be deduced from the sequence of the polypeptide according to the invention and codon usage may be adapted according to the host cell in which the nucleic acid shall be transcribed. These steps may be carried out according to methods well known to one of skill in the art and some of which are described in the reference manual Sambrook et al. (Sambrook J, Russell D (2001) Molecular cloning: a laboratory manual, Third Edition Cold Spring Harbor).

In a first embodiment, the nucleic acid of the invention comprises, or consists of, a nucleotide sequence having at least 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% identity to SEQ ID NO: 2. Preferably, the percentage of identity is determined over more than 10% of length of SEQ ID NO: 2, more preferably over more than 20, 30, 40, 50, 60, 70, 80, 90, 95, 99 or 100% of length of SEQ ID NO: 2. In a particular embodiment, the nucleic acid comprises, or consists of, the amino acid sequence of SEQ ID NO: 2.

In a second embodiment, the nucleic acid of the invention comprises, or consists of, a nucleotide sequence having at least 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% identity to SEQ ID NO: 4. Preferably, the percentage of identity is determined over more than 10% of length of SEQ ID NO: 4, more preferably over more than 20, 30, 40, 50, 60, 70, 80, 90, 95, 99 or 100% of length of SEQ ID NO: 4. In a particular embodiment, the nucleic acid comprises, or consists of, the amino acid sequence of SEQ ID NO: 4.

In a third embodiment, the nucleic acid of the invention comprises, or consists of, a nucleotide sequence having at least 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% identity to SEQ ID NO: 6. Preferably, the percentage of identity is determined over more than 10% of length of SEQ ID NO: 6, more preferably over more than 20, 30, 40, 50, 60, 70, 80, 90, 95, 99 or 100% of length of SEQ ID NO: 6. In a particular embodiment, the nucleic acid comprises, or consists of, the amino acid sequence of SEQ ID NO: 6.

The present invention also relates to an expression cassette comprising a coding region comprising a nucleic acid encoding at least one polypeptide according to the invention, operably linked to one or more control sequences that direct the expression of said coding region in a suitable host cell under conditions compatible with the control sequences.

The term "expression cassette" denotes a nucleic acid construct comprising a coding region, i.e. one or several genes, and a regulatory region, i.e. comprising one or more control sequences, operably linked. Optionally, the expression cassette may comprise several coding regions operably linked to several regulatory regions. In particular, the expression cassette may comprise several coding sequences, each of these sequences being operably linked to the same promoter or to a distinct promoter. Alternatively, the expression cassette may comprise one or several coding sequences, each of these sequences operably linked to a distinct promoter, and several other coding sequences operably linked to a common promoter.

The term "control sequences" means nucleic acid sequences necessary for expression of a coding region. Control sequences may be endogenous or heterologous. Well-known control sequences and currently used by the person skilled in the art will be preferred. Such control sequences include, but are not limited to, a leader, polyadenylation sequence, propeptide sequence, promoter, signal peptide sequence, and transcription terminator. Preferably, the control sequences include a promoter and a transcription terminator.

The term "operably linked" means a configuration in which a control sequence is placed at an appropriate position relative to a coding sequence, in such a way that the control sequence directs expression of the coding region.

The control sequence may include a promoter that is recognized by a host cell or an in vitro expression system for expression of a nucleic acid encoding a polypeptide of the invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either endogenous or heterologous to the host cell. The promoter may be an endogenous or heterologous promoter. The promoter may be a strong, weak, constitutive or inducible promoter. In a particular embodiment, the promoter is heterologous to the nucleic acid encoding a polypeptide of the invention, i.e. is not operably linked in nature to said nucleic acid or is operably linked at a different location in nature.

Preferably, the promoter is a polynucleotide that shows transcriptional activity in *Deinococcus* bacteria. In this regard, various promoters have been studied and used for gene expression in *Deinococcus* bacteria. Examples of suitable promoters include PtufA and PtufB promoters from the translation elongation factors Tu genes tufA (DR0309) and tufB (DR2050), the promoter of the resU gene located in pI3, the promoter region PgroESL of the groESL operon (Lecointe, et al. 2004. Mol Microbiol 53: 1721-1730 ; Meima et al. 2001. J Bacteriol 183: 3169-3175), or derivatives thereof.

The control sequence may also be a transcription terminator, which is recognized by a host cell to terminate transcription. The terminator is operably linked to the 3'-terminus of the nucleic acid encoding the polypeptide. Any terminator that is functional in the host cell may be used in the present invention. Preferably, the terminator is functional in *Deinococcus* bacteria. Examples of such terminator are disclosed in Lecointe et al, 2004, supra. Usually, the terminator is chosen in correlation with the promoter.

The control sequence may also be a signal peptide coding sequence that encodes a signal peptide linked to the N-terminus of an encoded polypeptide and directs the polypeptide into the cell's secretory pathway, i.e. for secretion into the extracellular (or periplasmic) space.

The coding region of the expression cassette may comprise (i) a nucleic acid encoding a polypeptide according to the invention and exhibiting L-arabinose isomerase activity, preferably a polypeptide comprising, or consisting of, the amino acid sequence of SEQ ID NO:1, (ii) a nucleic acid encoding a polypeptide according to the invention and exhibiting L-ribulokinase isomerase activity, preferably a polypeptide comprising, or consisting of, the amino acid sequence of SEQ ID NO:3, and/or (iii) a nucleic acid encoding a polypeptide according to the invention and exhibiting L-ribulose-5-phosphate 4 epimerase activity, preferably a polypeptide comprising, or consisting of, the amino acid sequence of SEQ ID NO:5.

In a particular embodiment, the coding region comprises a nucleic acid encoding a polypeptide according to the invention and exhibiting L-arabinose isomerase activity, and a nucleic acid encoding a polypeptide according to the invention and exhibiting L-ribulokinase isomerase activity.

In another embodiment, the coding region comprises a nucleic acid encoding a polypeptide according to the invention and exhibiting L-arabinose isomerase activity, and a nucleic acid encoding a polypeptide according to the invention and exhibiting L-ribulose-5-phosphate 4 epimerase activity.

In a further embodiment, the coding region comprises a nucleic acid encoding a polypeptide according to the invention and exhibiting L-ribulokinase isomerase activity, and a nucleic acid encoding a polypeptide according to the invention and exhibiting L-ribulose-5-phosphate 4 epimerase activity.

In a preferred embodiment, the coding region comprises a nucleic acid encoding a polypeptide according to the invention and exhibiting L-arabinose isomerase activity, a nucleic acid encoding a polypeptide according to the invention and exhibiting L-ribulokinase isomerase activity, and a nucleic acid encoding a polypeptide according to the invention and exhibiting L-ribulose-5-phosphate 4 epimerase activity.

The nucleic acids encoding the polypeptides according to the invention may be placed in any order in the coding region.

Preferably, the coding sequences comprised in the coding region are placed under the control of a same promoter, i.e. are placed in an operon. The nucleic acids encoding the polypeptides according to the invention may be placed in any order in the operon.

In a particular embodiment, the nucleic acids encoding the polypeptides according to the invention may be placed in the coding region or operon in the same order than in FIG. 1, i.e. a nucleic acid encoding a L-ribulokinase isomerase, a nucleic acid encoding a L-ribulose-5-phosphate 4 epimerase and a nucleic acid encoding a L-arabinose isomerase.

Optionally, the expression cassette may also comprise a selectable marker that permits easy selection of recombinant host cells. Typically, the selectable marker is a gene encoding antibiotic resistance or conferring autotrophy.

The expression cassette of the invention may be used directly to transform a host cell, preferably a *Deinococcus* host cell, and enable the expression of the nucleic acid of the invention in said cell. Preferably, the expression cassette, or a part thereof comprising a nucleic acid of the invention, is inserted in the genome of the host cell. In a particular embodiment, the expression cassette is integrated in the genome of the host cell, preferably a *Deinococcus* host cell. The expression cassette may be integrated, for example, in the gene encoding phosphoacetyltransferase (pta) or lactate dehydrogenase (ldh) or into an IS sequence present in the genome of the host cell (see e.g. WO 2015/092013).

The present invention also relates to an expression vector comprising a nucleic acid or an expression cassette according to the invention.

As used herein, the term "expression vector" means a DNA or RNA molecule that comprises an expression cassette. Preferably, the expression vector is a linear or circular double stranded DNA molecule.

The expression vector of the invention may be used to transform a host cell, preferably a *Deinococcus* host cell, and enable the expression of the nucleic acid of the invention in said cell. The choice of the vector will typically depend on the compatibility of the vector with the host cell into which the vector is to be introduced. The vector may be an autonomously replicating vector, i.e., a vector that exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one that, when introduced into the host cell, is integrated into the genome and replicated together with the chromosome(s) into which it has been integrated. Preferably, the vector, or a part thereof comprising a nucleic acid of the invention, e.g. the expression cassette of the invention, is inserted in the genome of the host cell. In a particular embodiment, the vector or expression cassette is integrated in the genome of the host cell, preferably a *Deinococcus* host cell, in the gene encoding phosphoacetyltransferase (pta) or lactate dehydrogenase (ldh). Alternatively, the vector or expression cassette may be integrated into an IS sequence present in the genome of the host cell (see e.g. WO 2015/092013).

The vector preferably comprises one or more selectable markers that permit easy selection of host cells comprising the vector. A selectable marker is a gene the product of which provides for antibiotic resistance, resistance to heavy metals, prototrophy to auxotrophy, and the like.

The vector preferably comprises an element that permits integration of the vector into the host cell's genome or autonomous replication of the vector in the cell independent of the genome. When integration into the host cell genome occurs, integration of the sequences into the genome may rely on homologous or non-homologous recombination. In one hand, the vector may contain additional polynucleotides for directing integration by homologous recombination at a precise location into the genome of the host cell. These additional polynucleotides may be any sequence that is homologous with the target sequence in the genome of the host cell. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell.

The methods for selecting these elements according to the host cell in which expression is desired, are well known to one of skill in the art. The vectors may be constructed by the classical techniques of molecular biology, well known to one of skill in the art.

The present invention further relates to the use of a nucleic acid, an expression cassette or an expression vector according to the invention to transform, transfect or transduce a cell.

It also relates to the use of a nucleic acid, an expression cassette or an expression vector according to the invention to confer an ability to ferment arabinose to a recombinant host cell.

The present invention also relates to a host cell, preferably a recombinant host cell, comprising a nucleic acid, an expression cassette or an expression vector according to the invention.

As used herein, the term "recombinant host cell" designates a cell that is not found in nature and which contains a modified genome as a result of either a deletion, insertion or modification of genetic elements. In a particular embodiment, this term refers to a cell comprising a "recombinant nucleic acid", i.e. a nucleic acid which has been engineered and is not found as such in the wild type cell.

In a particular embodiment, the recombinant host cell comprises a heterologous nucleic acid, i.e. a nucleic acid that does not naturally occur in said cell, in particular a heterologous nucleic acid encoding a polypeptide of the invention, or an expression cassette or vector comprising said nucleic acid.

The host cell may be transformed, transfected or transduced in a transient or stable manner. An expression cassette or vector of the invention is introduced into a host cell so that the cassette or vector is maintained as a chromosomal integrant or as a self-replicating extra-chromosomal vector as described earlier. The term "host cell" also encompasses any progeny of a parent host cell that is not identical to the parent host cell due to mutations that occur during replication.

The nucleic acid, expression cassette or expression vector according to the invention may be introduced into the host cell by any method known by the skilled person, such as electroporation, conjugation, transduction, competent cell transformation, protoplast transformation, protoplast fusion, biolistic "gene gun" transformation, PEG-mediated transformation, lipid-assisted transformation or transfection, chemically mediated transfection, lithium acetate-mediated transformation or liposome-mediated transformation.

Optionally, more than one copy of a nucleic acid, cassette or vector of the present invention may be inserted into the host cell to increase production of the polypeptide.

The host cell may be a prokaryote or eukaryote cell.

The prokaryotic host cell may be any Gram-positive or Gram-negative bacterium. Examples of suitable bacterial expression hosts include, but are not limited to, *Deinococcus* and related bacteria, *Escherichia* (e.g. *Escherichia coli*), *Pseudomonas* (e.g. *P. fluorescens* or *P. stutzeri*), *Proteus* (e.g. *Proteus mirabilis*), *Ralstonia* (e.g. *Ralstonia eutropha*), *Streptomyces*, *Staphylococcus* (e.g. *S. carnosus*), *Lactococcus* (e.g. *L. lactis*), or *Bacillus* (*subtilis*, *megaterium*, *licheniformis*, etc.).

The host cell may also be a eukaryotic cell, such as a yeast, fungal, mammalian, insect or plant cell. Examples of suitable yeast expression hosts include, but are not limited to, *Saccharomyces* (e.g. *Saccharomyces cerevisiae*, *Saccharomyces carlsbergensis*, *Saccharomyces diastaticus*, *Saccharomyces douglasii*, *Saccharomyces kluyveri*, *Saccharomyces norbensis*, *Saccharomyces oviformis*), *Schizosaccharomyces* (e.g. *Schizosaccharomyces pombe*), *Yarrowia* (e.g. *Yarrowia lipolytica*), *Hansenula* (e.g. *Hansenula polymorpha*), *Kluyveromyces* (e.g. *Kluyveromyces lactis*), *Pichia* (e.g. *Pichia pastoris*) or *Candida* cell.

Examples of suitable fungal expression hosts include, but are not limited to, *Trichoderma*, *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium* or *Trametes* cell.

Preferably, the host cell is a bacterium, more preferably a *Deinococcus* bacterium or related bacterium.

In the context of the invention, the term "*Deinococcus*" includes wild type or natural variant strains of *Deinococcus*, e.g., strains obtained through accelerated evolution, by DNA-shuffling technologies, mutagenesis or recombinant strains obtained by insertion of eukaryotic, prokaryotic and/or synthetic nucleic acid(s), strains genetically and/or chemically modified by any process known per se in the art or any genetic engineering technology. *Deinococcus* bacteria can designate any bacterium of the genus *Deinococcus*, such as without limitation, *D. geothermalis*, *D. cellulolysiticus*, *D. radiodurans*, *D. proteolyticus*, *D. radiopugnans*, *D. radiophilus*, *D. grandis*, *D. indicus*, *D. frigens*, *D. saxicola*, *D. maricopensis*, *D. marmoris*, *D. deserti*, *D. murrayi*, *D. aerius*, *D. aerolatus*, *D. aerophilus*, *D. aetherius*, *D. alpinitundrae*, *D. altitudinis*, *D. apachensis*, *D. aquaticus*, *D. aquatilis*, *D. aquiradiocola*, *D. aquivivus*, *D. caeni*, *D. claudionis*, *D. daejeonensis*, *D. depolymerans*, *D. ficus*, *D. gobiensis*, *D. hohokamensis*, *D. hopiensis*, *D. misasensis*, *D. navajonensis*, *D. papagonensis*, *D. peraridilitoris*, *D. pimensis*, *D. piscis*, *D. radiomollis*, *D. reticulitermitis*, *D. roseus*, *D. sonorensis*, *D. wulumuqiensis*, *D. xibeiensis*, *D. xinjiangensis*, *D. yavapaiensis*, *D. citri*, *D. guilhemensis*, *D. phoenicis*, *D. soli*, *D humi*, *D. sahariens*, *D. mumbaiensis*, or *D. yunweiensis* bacterium, or any combinations thereof. Preferably, the term "*Deinococcus*" refers to *D. geothermalis*, *D. cellulolysiticus*, *D. deserti*, *D. murrayi*, *D. maricopensis*, *D. aquatilis*, *D. gobiensis* or *D. radiodurans*. More preferably, the term "*Deinococcus*" refers to *D. geothermalis*, *D. cellulolysiticus*, *D. deserti*, *D. murrayi*, *D. maricopensis* or *D. radiodurans*.

In preferred embodiments, the host cell is a *Deinococcus* bacterium which is not naturally able to assimilate or utilize L-arabinose, i.e. which is not able to assimilate or utilize L-arabinose before introduction of a nucleic acid, expression cassette or vector of the present invention.

As used herein, the term "utilize" or "assimilate" refers to the capacity of an organism to use L-arabinose as a carbon source or energy source, in particular to produce a compound of interest.

As used herein, the term "related bacterium" refers to a bacterium "related" to *Deinococcus*, i.e. a bacterium which (i) contains a 16S rDNA which, upon amplification using primers GTTACCCGGAATCACTGGGCGTA (SEQ ID NO: 7) and GGTATCTACGCATTCCACCGCTA (SEQ ID NO: 8), generates a fragment of about 158 base pairs and/or (ii) resists a UV treatment of 4 mJ/cm$^2$. In a particular embodiment, *Deinococcus*-related bacteria are bacteria having a 16S rDNA molecule which is at least 70%, preferably at least 80% identical in sequence to a *Deinococcus* 16S rDNA sequence. In particular, the term "related bacterium" may refer to a *Deinobacterium*, *Truepera*, *Thermus*, *Meiothermus*, *Marinithermus*, *Oceanithermus*, *Vulcanithermus*, *Bacillus*, *Microbacterium*, *Cellulosimicrobium*, *Methylobacterium*, *Sphingobacterium*, *Pseudomonas*, *Caldimonas*, *Paenibacillus*, *Gordonia*, *Rhodococcus*, *Stenotrophomonas*, *Novosphingobium*, *Sphingomonas*, *Flavobacterium*, *Sphin-*

*gobium, Sphingopyxis, Tepidimonas, Exiguobacterium, Nocardia, Arthrobacter, Kineococcus, Williamsia, Porphyrobacter, Geodermatophylus, Hymenobacter, Kineococcus, Kocuria, Methylobacterium, Halobacterium salinarum, Chroococcidiopsis, Pyrococcus abissi* or *Lactobacillus plantarum* bacterium. Preferably, this term refers to a bacterium belonging to the phylum of *Deinococcus-Thermus* such as *Deinobacterium, Truepera, Thermus, Meiothermus, Marinithermus, Oceanithermus* or *Vulcanithermus* bacteria.

The host cell may express (i) a polypeptide comprising an amino acid sequence having at least 72% identity to SEQ ID NO: 1 and exhibiting L-arabinose isomerase activity, or a functional fragment thereof, preferably a polypeptide comprising, or consisting of, the amino acid sequence of SEQ ID NO:1, (ii) a polypeptide comprising an amino acid sequence having at least 73% identity to SEQ ID NO: 3 and exhibiting L-ribulokinase activity, or a functional fragment thereof, preferably a polypeptide comprising, or consisting of, the amino acid sequence of SEQ ID NO:3, or (iii) a polypeptide comprising an amino acid sequence having at least 73% identity to SEQ ID NO: 5 and exhibiting L-ribulose-5-phosphate 4 epimerase activity, or a functional fragment thereof, preferably a polypeptide comprising, or consisting of, the amino acid sequence of SEQ ID NO:5.

In a particular embodiment, the host cell expresses a polypeptide according to (i) and further exhibits L-ribulokinase activity and/or L-ribulose-5-phosphate 4 epimerase activity, preferably L-ribulokinase activity and L-ribulose-5-phosphate 4 epimerase activity.

In another particular embodiment, the host cell expresses a polypeptide according to (ii) and further exhibits L-arabinose isomerase activity and/or L-ribulose-5-phosphate 4 epimerase activity, preferably L-arabinose isomerase activity and L-ribulose-5-phosphate 4 epimerase activity.

In a further particular embodiment, the host cell expresses a polypeptide according to (iii) and further exhibits L-arabinose isomerase activity and/or L-ribulokinase activity, preferably L-arabinose isomerase activity and L-ribulokinase activity.

In an embodiment, the host cell expresses a polypeptide according to (i) and a polypeptide according to (ii). Preferably, the host cell further exhibits L-ribulose-5-phosphate 4 epimerase activity.

In another embodiment, the host cell expresses a polypeptide according to (i) and a polypeptide according to (iii). Preferably, the host cell further exhibits L-ribulokinase activity.

In another embodiment, the host cell expresses a polypeptide according to (ii) and a polypeptide according to (iii). Preferably, the host cell further exhibits L-arabinose isomerase activity.

In a preferred embodiment, the host cell expresses a polypeptide according to (i), a polypeptide according to (ii) and a polypeptide according to (iii).

In particular, the recombinant host cell may comprise a heterologous nucleic acid sequence encoding a polypeptide comprising an amino acid sequence having at least 72% identity to SEQ ID NO: 1 and exhibiting L-arabinose isomerase activity, or a functional fragment thereof, a heterologous nucleic acid sequence encoding a polypeptide comprising an amino acid sequence having at least 73% identity to SEQ ID NO: 3 and exhibiting L-ribulokinase activity, or a functional fragment thereof; and/or a heterologous nucleic acid sequence encoding a polypeptide comprising an amino acid sequence having at least 73% identity to SEQ ID NO: 5 and exhibiting L-ribulose-5-phosphate 4 epimerase activity, or a functional fragment thereof.

Said heterologous nucleic acids may be comprised in one or several expression cassettes or vectors. In particular, the recombinant host cell may comprise an expression cassette or vector comprising a nucleic acid encoding a polypeptide according to the invention and exhibiting L-arabinose isomerase activity, preferably a polypeptide comprising, or consisting of, the amino acid sequence of SEQ ID NO:1, and/or an expression cassette or vector comprising a nucleic acid encoding a polypeptide according to the invention and exhibiting L-ribulokinase isomerase activity, preferably a polypeptide comprising, or consisting of, the amino acid sequence of SEQ ID NO:3, and/or an expression cassette or vector comprising a nucleic acid encoding a polypeptide according to the invention and exhibiting L-ribulose-5-phosphate 4 epimerase activity, preferably a polypeptide comprising, or consisting of, the amino acid sequence of SEQ ID NO:5.

The host cell may also express one or several additional enzymes useful in the conversion of biomass, such as amylolytic, cellulolytic or hemicellulolytic enzymes. These additional enzymes may be endogenous or heterologous enzymes. These enzymes may be, for example, amylases, laccases, glucosidases, cellulases, xylanases, pectinases, esterases, acetyl xylan esterases, ferulic acid esterase, p-coumaroyl esterases, alpha-arabinofuranosidase, beta-galactosidases, mannanase, mannosidase and/or glucuronidases.

The host cell may also express endogenous or heterologous enzymes involved in production of compounds of interest by fermentation of monomeric sugars.

In a particular embodiment, the host cell expresses an endogenous or heterologous enzyme selected from acetaldehyde dehydrogenases, alcohol dehydrogenases (ADH) and/or pyruvate decarboxylase (PDC). Preferably, the host cell is a *Deinococcus* bacterium capable of producing ethanol, i.e. expressing endogenous or heterologous alcohol dehydrogenases (ADH) and pyruvate decarboxylase (PDC). This host cell is thus particularly useful for ethanol production from arabinose containing substrate.

In another particular embodiment, the host cell is capable of producing an isoprenoid compound, e.g. expresses endogenous or heterologous terpene synthase. Preferably, said host cell is a *Deinococcus* bacterium. This host cell is thus particularly useful for production of an isoprenoid compound from arabinose containing substrate.

In a further aspect, the present invention also relates to a recombinant *Deinococcus* bacterium or related bacterium comprising a heterologous nucleic acid sequence encoding a polypeptide exhibiting L-arabinose isomerase activity, a polypeptide exhibiting L-ribulokinase activity, and/or a polypeptide exhibiting L-ribulose-5-phosphate 4 epimerase activity.

Heterologous nucleic acid sequence(s) may be present in the bacteria, or inserted into the genome of the bacteria, in one or several copies.

In a particular embodiment, the recombinant bacterium is a *Deinococcus* bacterium selected from the group consisting of *D. geothermalis, D. cellulolysiticus, D. deserti, D. murrayi, D. aquatilis, D. gobiensis, D. maricopensis* and *D. radiodurans*. In another particular embodiment, the recombinant bacterium is a *Deinococcus* bacterium selected from the group consisting of *D. geothermalis, D. cellulolysiticus, D. deserti, D. murrayi, D. maricopensis* and *D. radiodurans*.

The nucleic acid sequence(s) may be selected from any nucleotide sequences known by the skilled person and encoding a polypeptide exhibiting L-arabinose isomerase activity, a polypeptide exhibiting L-ribulokinase activity, and/or a polypeptide exhibiting L-ribulose-5-phosphate 4 epimerase activity. Such sequences may be easily obtained from common databases such as GenBank or Uniprot.

In an embodiment, the recombinant bacterium comprises a heterologous nucleic acid sequence obtained from a *Deinococcus* strain and encoding a polypeptide exhibiting L-arabinose isomerase activity, a polypeptide exhibiting L-ribulokinase activity, and/or a polypeptide exhibiting L-ribulose-5-phosphate 4 epimerase activity.

In another embodiment, the recombinant bacterium comprises a heterologous nucleic acid sequence, preferably obtained from a *Deinococcus* strain, and encoding a polypeptide exhibiting L-arabinose isomerase activity, a heterologous nucleic acid sequence, preferably obtained from a *Deinococcus* strain, and encoding a polypeptide exhibiting L-ribulokinase activity, and/or a heterologous nucleic acid sequence, preferably obtained from a *Deinococcus* strain, and encoding a polypeptide exhibiting L-ribulose-5-phosphate 4 epimerase activity.

More preferably, the recombinant bacterium comprises one or several nucleic acid constructs, one or several expression cassettes and/or one or several expression vectors according to the invention, encoding one or several polypeptides of the invention. In particular, the recombinant bacterium may comprise a heterologous nucleic acid sequence encoding a polypeptide comprising an amino acid sequence having at least 72% identity to SEQ ID NO: 1 and exhibiting L-arabinose isomerase activity, or a functional fragment thereof, a heterologous nucleic acid sequence encoding a polypeptide comprising an amino acid sequence having at least 73% identity to SEQ ID NO: 3 and exhibiting L-ribulokinase activity, or a functional fragment thereof; and/or a heterologous nucleic acid sequence encoding a polypeptide comprising an amino acid sequence having at least 73% identity to SEQ ID NO: 5 and exhibiting L-ribulose-5-phosphate 4 epimerase activity, or a functional fragment thereof.

The present invention further relates to a cell extract of a host cell according to the invention.

As used herein, the term "cell extract" refers to any fraction obtained from a host cell, such as a cell supernatant, a cell debris, cell walls, DNA extract, enzymes or enzyme preparation or any preparation derived from host cells by chemical, physical and/or enzymatic treatment, which is essentially free of living cells.

The cell extract may comprise one or several polypeptides of the invention.

In particular, the cell extract may comprise
(i) a polypeptide comprising an amino acid sequence having at least 72% identity to SEQ ID NO: 1 and exhibiting L-arabinose isomerase activity, or a functional fragment thereof, preferably a polypeptide comprising, or consisting of, the amino acid sequence of SEQ ID NO:1,
(ii) a polypeptide comprising an amino acid sequence having at least 73% identity to SEQ ID NO: 3 and exhibiting L-ribulokinase activity, or a functional fragment thereof, preferably a polypeptide comprising, or consisting of, the amino acid sequence of SEQ ID NO:3, and/or
(iii) a polypeptide comprising an amino acid sequence having at least 73% identity to SEQ ID NO: 5 and exhibiting L-ribulose-5-phosphate 4 epimerase activity, or a functional fragment thereof, preferably a polypeptide comprising, or consisting of, the amino acid sequence of SEQ ID NO:5.

In an embodiment, the cell extract comprises a polypeptide according to (i) and a polypeptide according to (ii).

In another embodiment, the cell extract comprises a polypeptide according to (i) and a polypeptide according to (iii).

In another embodiment, the cell extract comprises a polypeptide according to (ii) and a polypeptide according to (iii).

In a preferred embodiment, the cell extract comprises a polypeptide according to (i), a polypeptide according to (ii) and a polypeptide according to (iii).

In another aspect, the present invention also relates to a method of producing a polypeptide of the invention, wherein the method comprises (a) culturing a host cell expressing said polypeptide, preferably a recombinant host cell of the invention, in conditions conducive for production of said polypeptide; and (b) recovering said polypeptide from the cell culture; and (c) optionally, purifying said polypeptide.

The host cell expressing a polypeptide of the invention, preferably a recombinant host cells of the invention, may be cultivated in a nutrient medium suitable for production of polypeptides using methods known in the art. For example, they may be cultivated by shake flask cultivation, or small-scale or large-scale fermentation (including continuous, batch, fed-batch, or solid state fermentations) in laboratory or industrial fermenters, performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection).

The polypeptide may be detected using any method known in the art. In particular, the polypeptide may be detected by any assay described above to assess L-arabinose isomerase, L-ribulokinase or L-ribulose-phosphate-4-epimerase activity, or, if the protein is a tagged recombinant protein, using antibodies directed against this tag with techniques well-known in the art.

The polypeptide may be recovered using any method known in the art. If the polypeptide of the invention is secreted into the nutrient medium, it can be recovered directly from the culture supernatant. If the polypeptide is not secreted, it can be recovered from cell lysates or after permeabilisation. For example, the polypeptide may be recovered from the nutrient medium by conventional procedures including, but not limited to, collection, centrifugation, filtration, extraction, spray-drying, evaporation, or precipitation.

Optionally, the polypeptide may be partially or totally purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction to obtain substantially pure polypeptides.

Alternatively, the method may comprise (a) contacting a nucleic acid, expression cassette or expression vector of the invention with an in vitro expression system; and (b) recovering the polypeptide; and (c) optionally, purifying said polypeptide. In vitro expression systems are well-known by the person skilled in the art and are commercially available.

In another aspect, the present invention also relates to a method for preparing a polypeptide of the invention immobilized on a solid support comprising producing the polypeptide as detailed above and immobilizing the polypeptide on a solid support. The present invention also relates to a solid support, a polypeptide according to the present invention being immobilized on the solid support. Immobilization means are well-known to the person skilled in the art (see e.g. 'Enzyme Technology' by Martin Chaplin and Christopher Bucke, Cambridge University Press, 1990). The polypeptide according to the present disclosure can be immobilized on the solid support by any convenient mean, in particular adsorption, covalent binding, entrapment or membrane confinement. A wide variety of insoluble materials may be used to immobilize the polypeptide. These are usually inert polymeric or inorganic matrices. The solid support can be for instance membranous, particulate or fibrous. More particularly, the solid support is preferably a bead, e.g., micro- or nanobeads. The polypeptide can be immobilized on a polyurethane matrix, on activated sepharose, alginate, amberlite resin, Sephadex resin or Duolite resin. Other solid supports useful for the invention include resins with an acrylic type structure, polystyrene resins, macroreticular resins and resins with basic functional groups. The immobilized polypeptide may then be used in a reactor. Examples of reactor include, but are not limited to, an enzyme reactor, a membrane reactor, a continuous flow reactor such as a stirred tank reactor, a continuously operated packed bed reactor, a continuously operated fluidized bed reactor, and a packed bed reactor.

Thus, in a further aspect, the present invention relates to a composition comprising at least one polypeptide of the invention as defined above and at least one additional enzyme.

The composition may comprise (i) a polypeptide comprising an amino acid sequence having at least 72% identity to SEQ ID NO: 1 and exhibiting L-arabinose isomerase activity, or a functional fragment thereof, preferably a polypeptide comprising, or consisting of, the amino acid sequence of SEQ ID NO:1, (ii) a polypeptide comprising an amino acid sequence having at least 73% identity to SEQ ID NO: 3 and exhibiting L-ribulokinase activity, or a functional fragment thereof, preferably a polypeptide comprising, or consisting of, the amino acid sequence of SEQ ID NO:3, and/or (iii) a polypeptide comprising an amino acid sequence having at least 73% identity to SEQ ID NO: 5 and exhibiting L-ribulose-5-phosphate 4 epimerase activity, or a functional fragment thereof, preferably a polypeptide comprising, or consisting of, the amino acid sequence of SEQ ID NO:5.

In an embodiment, the composition comprises a polypeptide according to (i) and a polypeptide according to (ii).

In another embodiment, the composition comprises a polypeptide according to (i) and a polypeptide according to (iii).

In another embodiment, the composition comprises a polypeptide according to (ii) and a polypeptide according to (iii).

In a preferred embodiment, the composition comprises a polypeptide according to (i), a polypeptide according to (ii) and a polypeptide according to (iii).

Preferably, said at least one additional enzyme is an enzyme involved in biomass conversion and may be selected, for example, from amylolytic, cellulolytic or hemicellulotic enzymes such as amylases, laccases, glucosidases, cellulases, xylanases, pectinases, esterases, acetyl xylan esterases, feruloyl esterase, p-coumaroyl esterases, alpha-arabinofuranosidase, beta-galactosidases, mannases, mannosidases and/or glucuronidases.

The composition may further comprise components suitable for enzyme preservation such as stabilisers like glycerol, sorbitol or monopropylene glycol, preservatives or buffering agents. The polypeptide(s) of the invention may be free or immobilized on a solid support. The composition can be liquid or dry. In a particular embodiment, the composition is liquid and comprises at least 10, 20, 30, 40 or 50% (w/v), preferably between 20 and 50% (w/v), of glycerol, sorbitol or monopropylene glycol, preferably glycerol.

The present invention also provides a composition comprising a recombinant host cell of the invention. The composition can be liquid (e.g. suspension) or dry (e.g. freeze-dried composition). Preferably, the composition comprising the host cell is kept frozen (e.g., at about −20° C.) until use. Preferably, the composition further comprises components suitable for cell preservation, in particular if cells are frozen. The composition of the invention may comprise one or several host cells of the invention, and optionally one or several additional cells.

The present invention also relates to a cosmetic composition comprising a recombinant host cell of the invention and/or a cell extract thereof. It further relates to the use of a recombinant host cell of the invention and/or a cell extract thereof, to prepare a cosmetic composition. In the context of the invention, cosmetic compositions, or beauty products, relate to compositions suitable for application on at least a part of the body, for cosmetic effects. Cosmetic compositions of the invention may include, but are not limited to, lotions, such as hair lotion and aftershave lotion, skin creams, such as day cream, anti-wrinkle cream and moisturizing cream, or make-up, such as lipstick, etc. The cosmetic composition of the invention may further contain one or more cosmetically acceptable carriers or diluents and/or one or more additional active ingredients.

The present invention also relates to a feed or food composition, a food additive or a dietary supplement, comprising, or consisting of, a recombinant host cell of the invention and/or a cell extract thereof. It further relates to the use of a recombinant host cell of the invention and/or a cell extract thereof, to prepare a feed or food composition, a food additive or a dietary supplement. Methods to produce such composition, additive or supplement are well-known by the skilled person, see e.g. WO 2013/092645. The food additive (i.e. an additive modifying the properties (e.g. nutritional, digestibility, palatability) of a food) may be added to a food before, during or after preparation of said food. In a particular embodiment, the composition, additive or supplement comprises a recombinant host cell of the invention and/or a cell extract thereof, and a cellulosic biomass, preferably an arabinose containing cellulosic biomass. Said biomass may be raw or pre-treated.

The present invention also relates to a composition comprising at least one polypeptide or recombinant host cell of the invention and an arabinose containing substrate as described below.

In a further aspect, the present invention relates to a method of producing a fermentation product comprising contacting a substrate, preferably cellulosic biomass, with a polypeptide of the invention, a host cell expressing said polypeptide or a recombinant host cell of the invention, and optionally recovering the fermentation production.

Preferably, the substrate is an arabinose containing substrate, more preferably an arabinose containing cellulosic biomass.

As used herein, the term "cellulosic biomass" refers to any biomass material, preferably vegetal biomass, comprising cellulose, hemicellulose and/or lignocellulose, preferably comprising cellulose and hemicellulose. Cellulosic biomass includes, but is not limited to, pectins and hemicellulosics (such as xylan) which contain mixtures of hexoses and pentoses (e.g. xylose, arabinose), plant material such as forestry products, woody feedstock (softwoods and hardwoods), agricultural wastes or agricultural by-products and plant residues or hydrolysates thereof (such as corn stover, corn cob, corn husk, corn fiber, oat, shorghum, sugarcane bagasse, grasses, rice straw, wheat straw, empty fruit bunch from oil palm and date palm, agave bagasse, from tequila industry), perennial grasses (switchgrass, miscanthus, canary grass, erianthus, napier grass, giant reed, and alfalfa); municipal solid waste (MSW), aquatic products such as algae and seaweed, wastepaper, leather, cotton, hemp, natural rubber products, by-products from paper and pulp industry such as spent liquor and wood hydrolysates, sugar beet and food processing by-products.

Preferably, if the cellulosic biomass comprises lignocellulose, this biomass is pre-treated before use in the method of the invention. This pretreatment is intended to open the bundles of lignocelluloses in order to access the polymer chains of cellulose and hemicellulose. Pretreatment methods are well known by the skilled person and may include physical pretreatments (e.g. high pressure steaming, extrusion, pyrolysis or irradiation), physicochemical and chemical pretreatments (e.g. ammonia fiber explosion, treatments with alkaline, acidic, solvent or oxidizing agents) and/or biological pretreatments.

Arabinose may be contained in the substrate as monomeric or polymeric arabinose, or as a constituent of heteropolysaccharides typically further containing galactose, rhamnose, mannose, glucose, galacturonic acid, glucuronic acid, 4-o-methyl glucuronic acid, xylose and/or ferulic acid.

In a preferred embodiment, the substrate is an arabinose-rich substrate, preferably an arabinose rich biomass and more preferably an arabinose rich cellulosic biomass. The arabinose-rich substrate may also be an arabinose-rich polymer.

As used herein the term "arabinose-rich polymer" refers to a polymer comprising at least 10% arabinose, preferably 20, 30, 40, 50, 60, 70, 80, 90, 95, 99 or 100% arabinose. Examples of such polymers include, but are not limited to, arabinans, pectin-arabinans, arabinogalactans and arabinoxylans.

As used herein, the term "arabinose rich substrate" refers to a substrate comprising at least 10% arabinose, preferably 20, 30, 40, 50, 60, 70, 80, 90, 95, 99 or 100% arabinose. The substrate may be a solid or liquid substrate, a partially or totally purified substrate or a raw substrate. As used herein, the term "arabinose rich biomass" refers to a biomass, preferably a cellulosic biomass, comprising at least 10% arabinose, preferably 20, 30, 40, 50 or 60% arabinose. Preferably, the percentage of arabinose refers to the percentage of dried matter, i.e. the term "10%" refers to 10 g of arabinose for 100 g of dried matter.

Examples of arabinose rich cellulosic biomasses include, but are not limited to, exudate gums from some tropical trees and bushes such as gum arabic, gum tragacanth and gum ghatti, pectin compounds such as sugar beet, chickory root, citrus pectin and apple pectin, algae, the araban of citrus fruit, the arabinogalactan of the larch tree as well as hardwood bark such as beech or birch bark, grain straw or hulls, corn husks, corn cobs, corn fibers and bagasse.

This biomass may be raw or pre-treated before to be used in the method of the invention.

The fermentation is a metabolic process carried out by a microorganism wherein monomeric sugars are converted to a product of interest, preferably a product of industrial interest. This metabolic pathway may be naturally encoded by the microorganism, or said microorganism may have been genetically engineered to carry out such pathway.

Examples of fermentation products of interest include, but are not limited to, biofuel such as ethanol, butanol, propanol, glycerol methanol, isopropanol, propanediol, glycerol or 2-3 butanediol, organic acids such as formate, acetate, lactate, butyrate, gluconate, xylonate, citrate, succinate, propionate, fumarate, malate, pyruvate, itaconic acid, muconic acid and kojic acid, and their salts or esters, isoprenoïd compounds such as geraniol, carotenoids, drug or pharmaceutical compounds such as antibiotics, bacteriostatic compounds, antimetabolite, chemotherapeutic compounds, anti-parasitic agents, anti-fungal agents, anti-viral compounds, cytokine-activity compounds, anti-oxidants or cell-growth factors. The fermentation product may also be a cosmetic or nutrient compound. Examples of cosmetic compounds include, but are not limited to anti-oxidants and carotenoids. Examples of nutrient compounds include, but are not limited to, vitamins, amino acids and fatty acids. Preferably, the fermentation product is a biofuel, more preferably ethanol, or an isoprenoid compound, more preferably a carotenoid compound. In a particular embodiment, the fermentation product is geraniol.

Depending on the conditions, the biomass or substrate can be contacted with a polypeptide of the invention, a host cell expressing said polypeptide or a recombinant host cell of the invention, or an extract thereof, alone or in combination with other enzymes or cells. It should be understood that the precise amounts of polypeptide or host cell used initially in order to efficiently transform biomass or substrate can be adjusted by the skilled artisan depending on the type of cells, the type of biomass or substrate, and the culture conditions.

In a particular embodiment, the method of the invention is performed in a reactor of conversion of biomass. By "reactor" is meant a conventional fermentation tank or any apparatus or system for biomass conversion, typically selected from bioreactors, biofilters, rotary biological contactors, and other gaseous and/or liquid phase bioreactors. The apparatus which can be used according to the invention can be used continuously or in batch loads. Depending on the cells used, the method may be conducted under aerobiosis, anaerobiosis or microaerobiosis.

Further aspects and advantages of the present invention will be described in the following examples, which should be regarded as illustrative and not limiting.

EXAMPLES

The inventors identified a novel L-arabinose pathway operon from *Deinococcus roseus* encoding L-ribulokinase (AraB), L-ribulose-5-phosphate 4-epimerase (AraD) and L-arabinose isomerase (AraA). They showed that the introduction and expression of this operon in *Deinococcus* strain confers the ability to utilize L-arabinose as sole carbon source. In addition, they showed that the introduction and expression of this operon in an ethanologenic *Deinococcus* strain confers the ability to produce ethanol from L-arabinose as sole carbon source. They further showed that the introduction of this L-arabinose pathway operon in a *Deinococcus* strain expressing the geraniol synthase from *Ocimum basilicum*, enables said bacterium to produce geraniol from L-arabinose as carbon source. They further showed that the recombinant *Deinococcus* strain containing the arabinose operon is able efficiently to co-assimilate arabinose, glucose and/or xylose without diauxie.

Materials and Methods

*Deinococcus* Strains

*Deinococcus roseus* was obtained from DSMZ collection under the following reference DSM-22367.

The *Deinococcus geothermalis* strain used in examples 1 to 3 is an ethanol-producing recombinant strain comprising a nucleic acid encoding a pyruvate decarboxylase (PDC) and an alcohol dehydrogenase (ADH) from *Zymomonas mobilis*. This strain was obtained as described in the international patent application WO 2010/130806.

The *Deinococcus geothermalis* strain used in example 4 is a recombinant strain comprising a nucleic acid encoding a geraniol synthase (GES) from *Ocimum basilicum*. The GES cDNA was inserted into the chromosome in replacement of the phosphotransacetylase (pta) gene. Expression of GES gene is under the control of a constitutive promoter. To increase isoprenoid production, this strain was engineered to also express a mutant farnesyl pyrophosphate synthase (K170G) and to overexpress DXS and IDI genes of the MEP pathway. This strain was obtained as described in international patent application WO 2015/189428.

Genomic DNA was prepared using Dneasy & Blood QIAGEN Kit as indicated by the Manufacturer.

The *D. roseus* arabinose operon encoding L-ribulokinase (AraB), L-ribulose-5-phosphate 4-epimerase (AraD) and L-arabinose isomerase (AraA,) was amplified and assembled with a constitutive promoter by overlapping PCR.

Insertion of DNA fragments into the chromosome of *Deinococcus geothermalis* was performed using homologous recombination mechanism. Insertion cassettes comprised a nucleic acid sequence to be inserted into the chromosome, flanked by 500 bp region homologous to the sequence upstream or downstream the chromosomic target.

For the expression of heterologous genes, strong constitutive promoters were used such as PtufA and PtufB promoters from the translation elongation factors Tu genes tufA (DR0309) and tufB (DR2050), or the promoter region PgroESL of the groESL operon (Lecointe et al, 2004; Meima et al, 2001).

The expression cassette containing the arabinose operon from *D. roseus* DSM-22367 with L-ribulokinase encoding gene (araB, SEQ ID NO: 4), L-ribulose-5-phosphate 4-epimerase encoding gene (araD, SEQ ID NO: 6) and L-arabinose isomerase encoding gene (araA, SEQ ID NO: 2) and an erythromycin resistance cassette, were inserted into the chromosome of the ethanol-producing and geraniol-producing *Deinococcus geothermalis* strains described above disrupting the ldh gene encoding lactate dehydrogenase.

Results

Example 1

Assimilation of L-arabinose and Production of Ethanol

The *Deinococcus roseus* arabinose operon encoding L-ribulokinase (AraB), L-ribulose-5-phosphate 4-epimerase (AraD) and L-arabinose isomerase (AraA) was inserted into the chromosome of the ethanol producing *Deinococcus geothermalis*, disrupting the lactate dehydrogenase (ldh) gene as described above.

The cultures of ethanol producing strains comprising or not the *D. roseus* L-arabinose operon were performed at 48° C. and 250 rpm for 48 h. These cultures were used to inoculate, at an initial optical density at 600 nm (OD600) of 0.4, 25 ml of a defined medium containing L-arabinose as sole carbon source. The composition of this defined medium was: $(NH_4)_2SO_4$ 100 mM; $NaH_2PO_4.H_2O$ 10 mM; KCl 10 mM; $Na_2SO_4$ 10 mM; citrate 30 mM; $MgCl_2.6H_2O$ 10 mM; $CaCl_2.2H_2O$ 10 mM; $ZnCl_2$ 50 mg/L; $FeSO_4.7H_2O$ 50 mg/L; $MnCl_2.4H_2O$ 50 mg/L; $CuSO_4$ 50 mg/L; $CoCl_2.6H_2O$ 50 mg/L; $H_3BO_3$ 5 mg/L; MES 200 mM; $(NH_4)_6Mo_7O_{24}.4H_2O$ 0.5 mM; Arabinose 30 g/L (200 mM).

Figure 2:
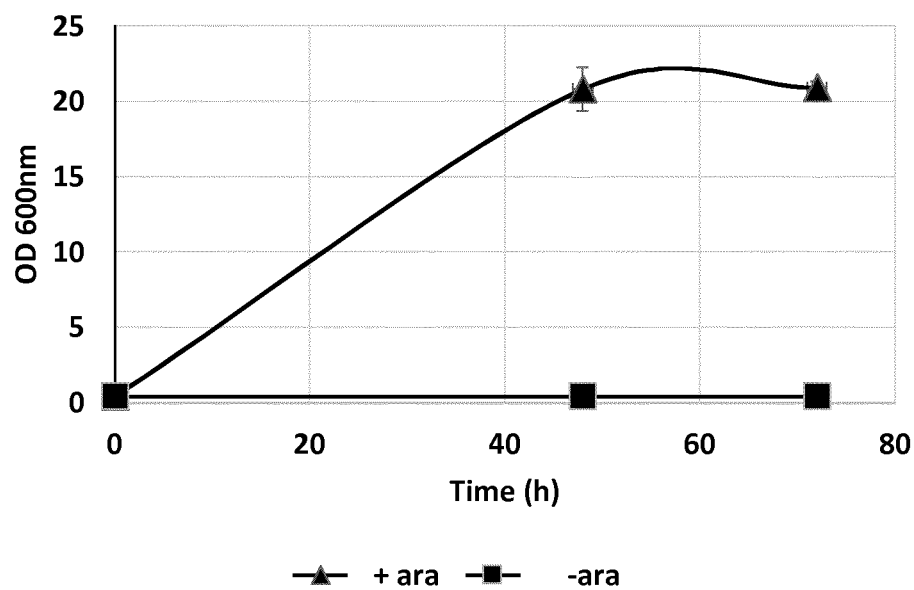
FIG. 2: Growth of *D. geothermalis* strain containing pdc and adh genes but not the arabinose operon (–ara) and the recombinant *D. geothermalis* strain containing pdc and adh genes and the *D. roseus* arabinose operon (+ara) on minimal defined medium containing L-arabinose as sole carbon source.
Figure 3:
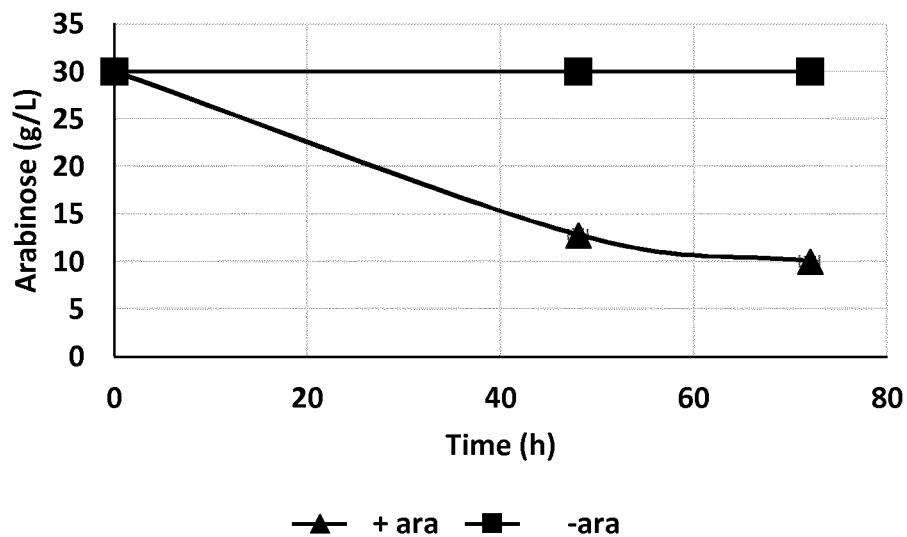
FIG. 3: Arabinose concentration in the medium during the growth of *D. geothermalis* strain containing pdc and adh genes but not the arabinose operon (–ara) and the recombinant *D. geothermalis* strain containing pdc and adh genes and the *D. roseus* arabinose operon (+ara) on minimal defined medium containing L-arabinose as sole carbon source.

After 48 h of culture, growth was observed only for the recombinant strain containing the L-arabinose assimilation operon (ara+) inserted into its chromosome (FIG. 2). The consumption of L-arabinose was followed during the growth and showed that 66% of total L-arabinose were consumed after 70 hours of growth (FIG. 3).

Figure 4:
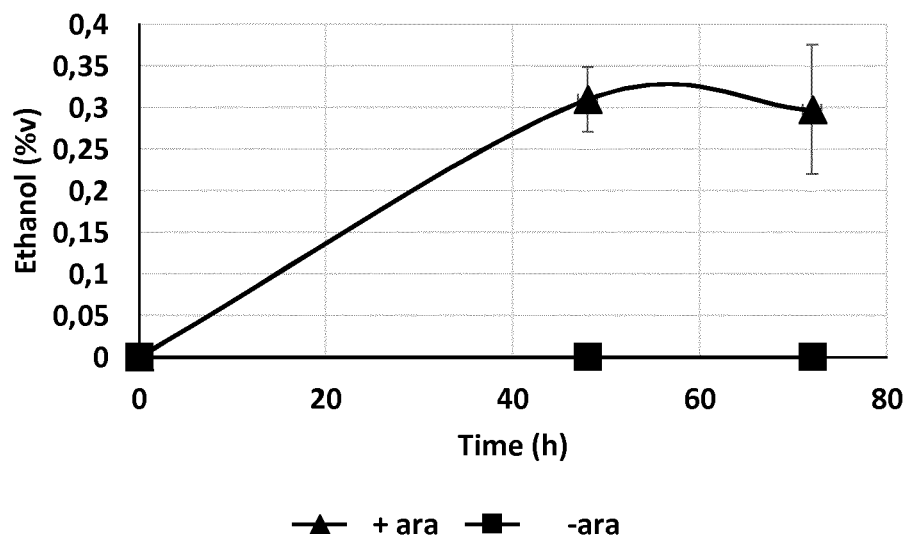
FIG. 4: Ethanol production during the growth of *D. geothermalis* strain containing pdc and adh genes but not the arabinose operon (–ara) and the recombinant *D. geothermalis* strain containing pdc and adh genes and the *D. roseus* arabinose operon (+ara) on minimal defined medium containing L-arabinose as sole carbon source.

The ethanol production was also measured during the growth. Ethanol production was observed only for the recombinant strain containing the L-arabinose assimilation operon inserted into its chromosome (FIG. 4).

These data clearly demonstrated that the *D. roseus* L-arabinose assimilation operon identified by the inventors encodes active enzymes and is sufficient to allow an ethanol-producer *Deinococcus* strain to grow and produce ethanol from L-arabinose.

Example 2

Co-Assimilation of Glucose and Arabinose

The cultures of the ethanol producing *D. geothermalis* strain comprising the L-arabinose assimilation pathway of *D. roseus* were performed at 48° C. and 250 rpm at an initial optical density at 600 nm (OD600) of 0.4 and in a mineral defined medium containing L-arabinose and glucose as carbon sources. The composition of the medium was: $(NH_4)_2SO_4$ 100 mM; $NaH_2PO_4.H_2O$ 10 mM; KCl 10 mM; $Na_2SO_4$ 10 mM; Acide citrique 30 mM; $MgCl_2.6H_2O$ 10 mM; $CaCl_2.2H_2O$ 10 mM; $ZnCl_2$ 50 mg/L; $FeSO_4.7H_2O$ 50 mg/L; $MnCl_2.4H_2O$ 50 mg/L; $CuSO_4$ 50 mg/L; $CoCl_2.6H_2O$ 50 mg/L; $H_3BO_3$ 5 mg/L; MES 200 mM; $(NH_4)_6Mo7O_{24}.4H_2O$ 0.5 mM; Arabinose 15 g/L (100 mM), Glucose 15 g/L (83 mM).

Figure 5:
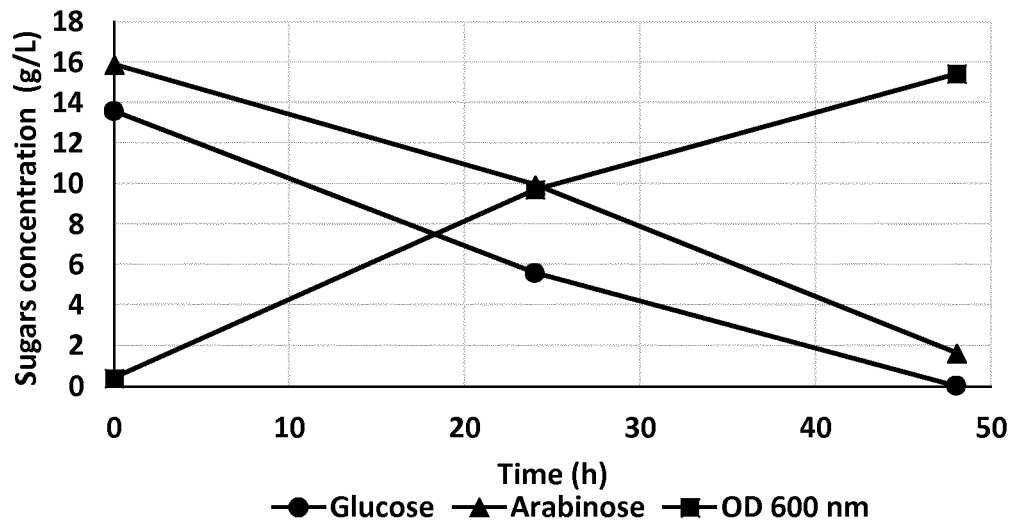
FIG. 5: Glucose and arabinose concentrations in the culture medium during the growth of the recombinant *D. geothermalis* strain containing pdc and adh genes and the *D. roseus* arabinose operon on minimal defined medium containing L-arabinose and glucose as sole carbon sources.
Figure 6:
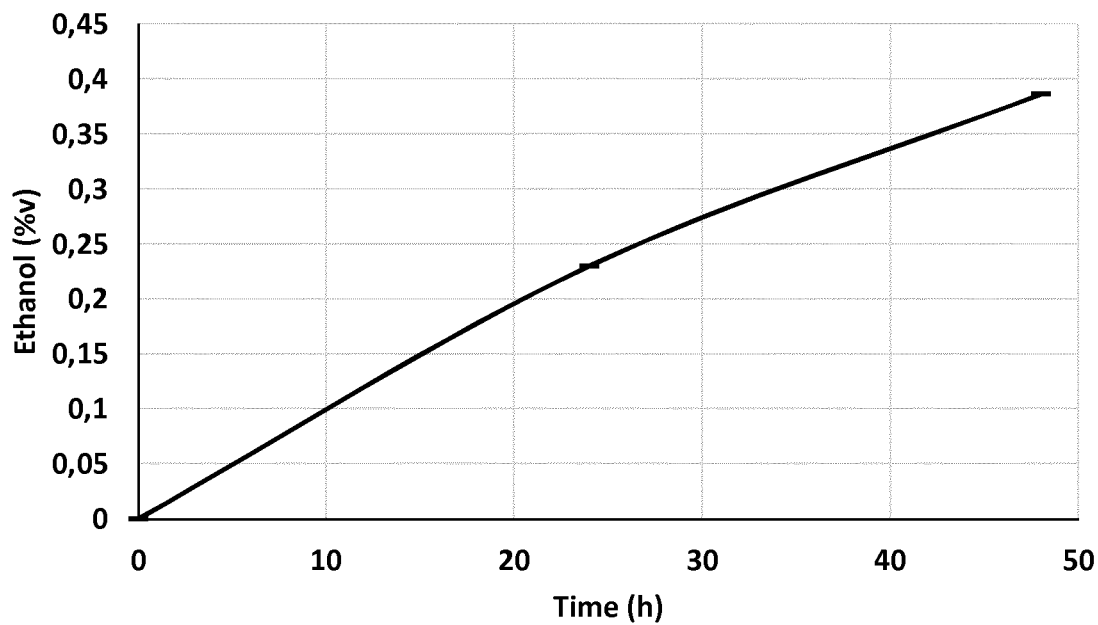
FIG. 6: Ethanol production during the growth of the recombinant *D. geothermalis* strain containing pdc and adh genes and the *D. roseus* arabinose operon on minimal defined medium containing L-arabinose and glucose as sole carbon sources.

Following the growth and the concentration of glucose and arabinose in the medium, the inventors showed that the recombinant *D. geothermalis* strain is able to co-assimilate glucose and arabinose (FIG. 5) and to produce ethanol at the same time (FIG. 6).

Example 3

Co-Assimilation of Glucose, Xylose and Arabinose

The cultures of the ethanol producing *D. geothermalis* strain comprising the L-arabinose assimilation pathway of *D. roseus* were performed at 48° C. and 250 for 48 h from log phase of growth and were inoculated into 25 ml of a technical medium obtained after dilute acid pre-treatment followed by an enzymatic hydrolysis of corn stover substrate. This medium comprised glucose (50%), xylose (25%) and arabinose (25%). Three different concentrations of this technical medium were used: 10% (glucose 18 mM, xylose 11 mM, arabinose 12 mM), 20% (glucose 35 mM, xylose 21 mM, arabinose 25 mM) and 30% (glucose 42 mM, xylose 33 mM, arabinose 35 mM).

Figure 7:
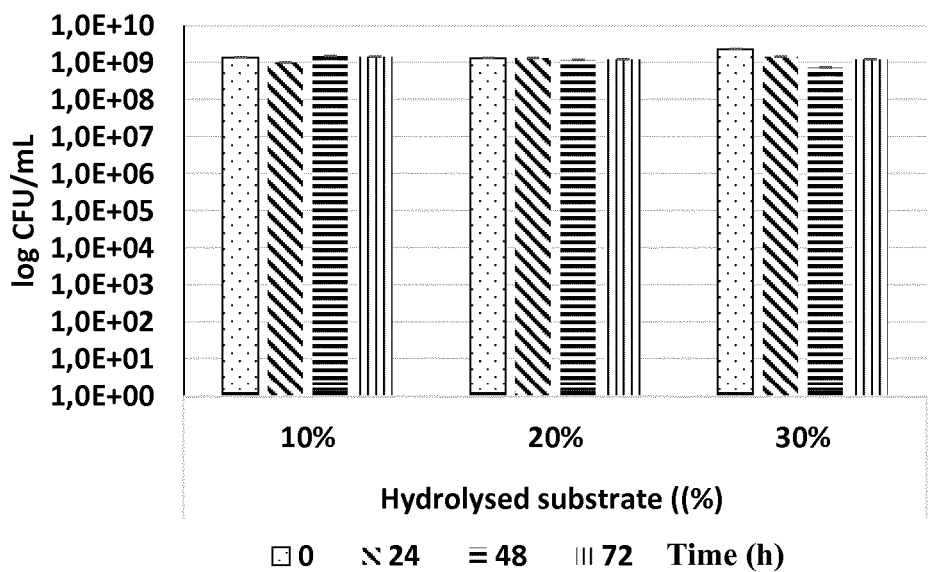
FIG. 7: Growth of the recombinant *D. geothermalis* strain containing pdc and adh genes and the *D. roseus* arabinose operon on a technical medium comprising 10%, 20% or 30% of a hydrolysate of corn stover substrate.
Figure 8:
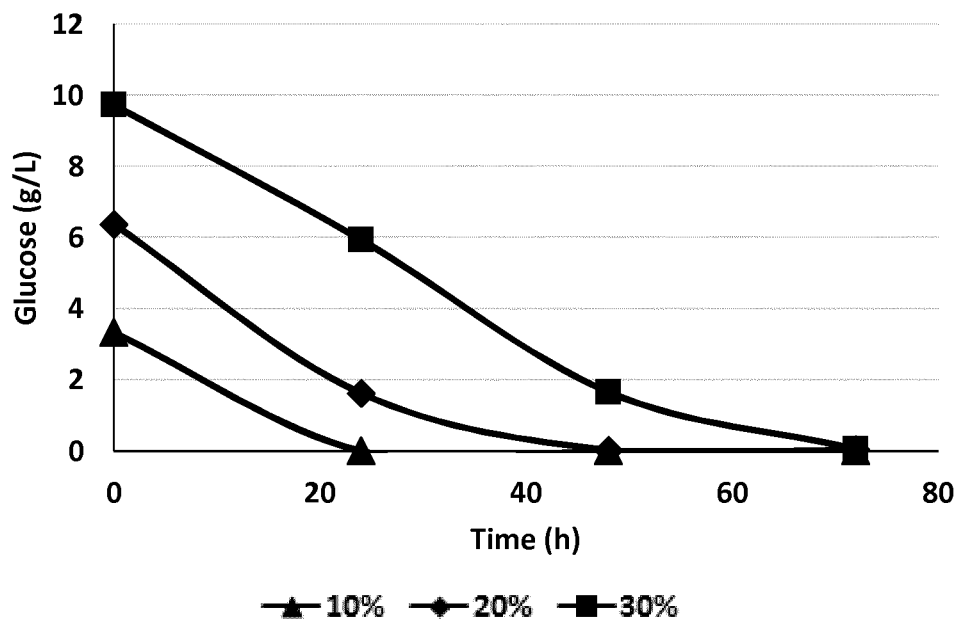
FIG. 8: Glucose concentration during the growth of the recombinant *D. geothermalis* strain containing pdc and adh genes and the *D. roseus* arabinose operon on a technical medium comprising 10%, 20% or 30% of a hydrolysate of corn stover substrate.
Figure 9:
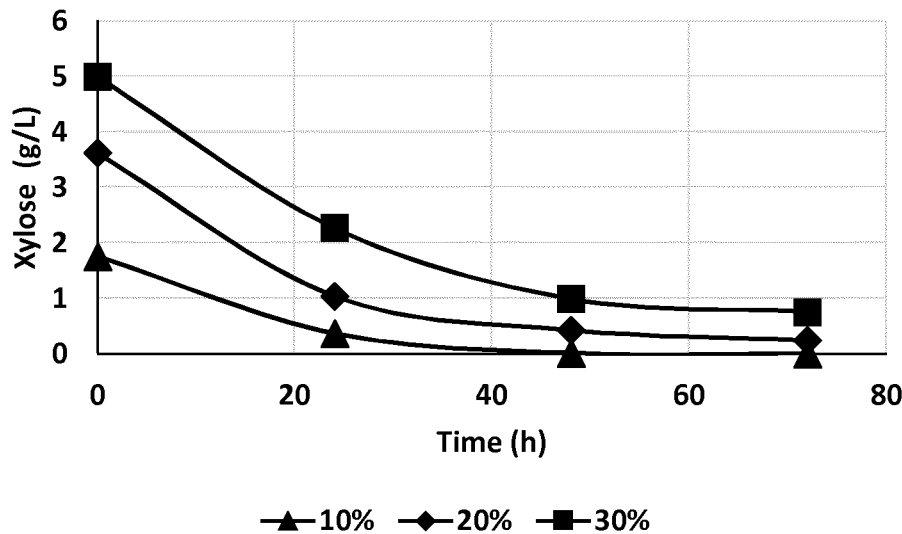
FIG. 9: Xylose concentration during the growth of the recombinant *D. geothermalis* strain containing pdc and adh genes and the *D. roseus* arabinose operon on a technical medium comprising 10%, 20% or 30% of a hydrolysate of corn stover substrate.
Figure 10:
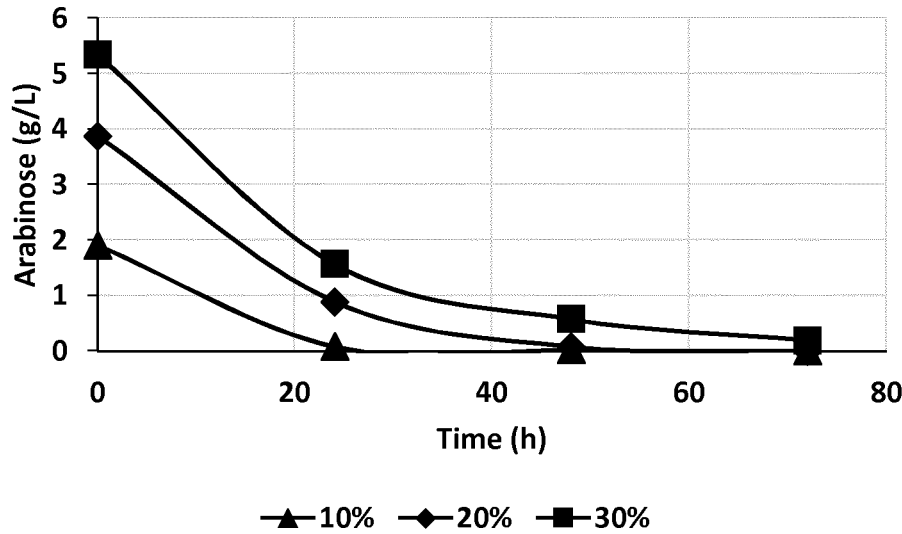
FIG. 10: Arabinose concentration during the growth of the recombinant *D. geothermalis* strain containing pdc and adh genes and the *D. roseus* arabinose operon on a technical medium comprising 10%, 20% or 30% of a hydrolysate of corn stover substrate.

Following the growth and the concentration of glucose, xylose and arabinose in the medium, the inventors showed that the recombinant *D. geothermalis* strain is able to co-assimilate glucose, xylose and arabinose (FIGS. 7 to 9).

Example 4

Assimilation of L-arabinose and Production of Geraniol

The *Deinococcus roseus* arabinose operon encoding L-ribulokinase (AraB), L-ribulose-5-phosphate 4-epimerase (AraD) and L-arabinose isomerase (AraA) was inserted into the chromosome of the geraniol-producing *Deinococcus geothermalis*, disrupting the lactate dehydrogenase (ldh) gene as described above.

To make seed cultures, individual colonies were picked to inoculate 25 ml of CMA2% medium (Peptone 2 g/L; Yeast Extract 5 g/L; Glucose 55 mM (20 g/L); MOPS acid 40 mM; $NH_4Cl$ 20 mM; NaOH 10 mM; KOH 10 mM; $CaCl_2.2H_2O$ 0.5 µM; $Na_2SO_4.10H_2O$ 0.276 mM; $MgCl_2.6H_2O$ 0.528 mM; $(NH_4)_6(Mo_7)O_{24}.4H_2O$ 3 nM; $H_3BO_3$ 0.4 µM; $CoCl_2.6H_2O$ 30 nM; $CuSO_4.5H_2O$ 10 nM; $MnCl_2$ 0.25 µM; $ZnSO_4.7H_2O$ 10 nM; D-Biotin 1 µg/L; Niacin (nicotinic acid) 1 µg/L; B6 vitamin 1 µg/L; B1 vitamin; $FeCl_3$ 20 µM; Sodium Citrate.$2H_2O$ 20 µM; $K_2HPO_4$ 5.7 mM) containing 2% arabinose as the main carbon source, and cultured at 37° C. and 250 rpm overnight. Seed from log phase of growth was then inoculated into 25 ml of the same fresh medium at an initial optical density at 600 nm (OD600) of 0.4. This second seed culture was cultured at 37° C. and 250 rpm overnight. The cultures for geraniol production were performed at 37° C. and 250 rpm for 48 h from log phase of growth inoculated into 25 ml of mineral define medium $(NH_4)_2SO_4$<100 mM ; $NaH_2PO_4.H_2O$<10 mM; KCl<10 mM; $Na_2SO_4$<10 mM; citric acid<30 mM; $MgCl_2.6H_2O$<10 mM; $CaCl_2.2H_2O$<10 mM; $ZnCl_2$<50 mg/L; $FeSO_4.7H_2O$<50 mg/L; $MnCl_2.4H_2O$<50 mg/L; $CuSO_4$<50 mg/L; $CoCl_2.6H_2O$<50 mg/L; $H_3BO_3$<5 mg/L; MES<200 mM; $(NH_4)_6Mo_7O_{24}.4H_2O$<0.5 mM; Arabinose 20 g/L at an initial optical density at 600 nm (OD600) of 0.4.

After 48 h of culture, growth was observed only for the recombinant strain containing the L-arabinose assimilation operon (ara+) inserted into its chromosome. The recombinant strain produced about 2.8 mg geraniol/g arabinose, or about 15 mg/L of geraniol after 48 h of culture.

These results showed that the *D. roseus* L-arabinose assimilation operon identified by the inventors enables a geraniol-producing strain to grow and produce geraniol from L-arabinose.

---

The invention claimed is:

1. A recombinant host cell comprising a heterologous nucleic acid construct, expression cassette or vector comprising:
   a nucleic acid sequence encoding a polypeptide comprising an amino acid sequence having at least 95% identity to SEQ ID NO: 5 and exhibiting L-ribulose-5-phosphate 4 epimerase activity, or a functional fragment thereof, and/or
   a nucleic acid sequence encoding a polypeptide comprising an amino acid sequence having at least 95% identity to SEQ ID NO: 1 and exhibiting L-arabinose isomerase activity, or a functional fragment thereof, and/or
   a nucleic acid sequence encoding a polypeptide comprising an amino acid sequence having at least 95% identity to SEQ ID NO: 3 and exhibiting L-ribulokinase activity, or a functional fragment thereof,
   wherein the functional fragment is at least 100 contiguous amino acids of said polypeptide, and retains the enzymatic activity of the entire polypeptide.

2. The recombinant host cell according to claim 1, wherein the heterologous nucleic acid construct, expression cassette or vector comprises a nucleic acid sequence encoding a polypeptide comprising an amino acid sequence having at least 95% identity to SEQ ID NO: 5 and exhibiting L-ribulose-5-phosphate 4 epimerase activity, or a functional fragment thereof which is at least 100 contiguous amino acids of said polypeptide and retains the enzymatic activity of the entire polypeptide.

3. The recombinant host cell according to claim 1, wherein the heterologous nucleic acid construct, expression cassette or vector comprises a nucleic acid sequence encoding a polypeptide comprising the amino acid sequence of SEQ ID NO: 5.

4. The recombinant host cell according to claim 1, wherein the heterologous nucleic acid construct, expression cassette or vector comprises a nucleic acid sequence encoding a polypeptide comprising an amino acid sequence having at least 95% identity to SEQ ID NO: 1 and exhibiting L-arabinose isomerase activity, or a functional fragment thereof which is at least 100 contiguous amino acids of said polypeptide and retains the enzymatic activity of the entire polypeptide.

5. The recombinant host cell according claim 1, wherein the recombinant nucleic acid construct, expression cassette or vector comprises a nucleic acid sequence encoding a polypeptide comprising an amino acid sequence having at least 98% identity to SEQ ID NO: 1 and exhibiting L-arabinose isomerase activity.

6. The recombinant host cell according to claim 1, wherein the heterologous nucleic acid construct, expression cassette or vector comprises a nucleic acid sequence encoding a polypeptide comprising the amino acid sequence of SEQ ID NO: 1.

7. The recombinant host cell according to claim 1, wherein the heterologous nucleic acid construct, expression cassette or vector comprises a nucleic acid sequence encoding a polypeptide comprising an amino acid sequence having at least 95% identity to SEQ ID NO: 3 and exhibiting L-ribulokinase activity, or a functional fragment thereof which is at least 100 contiguous amino acids of said polypeptide and retains the enzymatic activity of the entire polypeptide.

8. The recombinant host cell according to claim 1, wherein the heterologous nucleic acid construct, expression cassette or vector comprises a nucleic acid sequence encoding a polypeptide comprising an amino acid sequence having at least 98% identity to SEQ ID NO: 3 and exhibiting L-ribulokinase activity.

9. The recombinant host cell according to claim 1, wherein the heterologous nucleic acid construct, expression cassette or vector comprises a nucleic acid sequence encoding a polypeptide comprising the amino acid sequence of SEQ ID NO: 3.

10. The recombinant host cell according to claim 1, wherein the heterologous nucleic acid construct, expression cassette or vector comprises a nucleic acid sequence encoding a polypeptide comprising the amino acid sequence of SEQ ID NO: 1, a nucleic acid sequence encoding a polypeptide comprising the amino acid sequence of SEQ ID NO: 3 and a nucleic acid sequence encoding a polypeptide comprising the amino acid sequence of SEQ ID NO: 5.

11. The recombinant host cell according to claim 1, wherein the host cell is a *Deinococcus* bacterium.

12. The recombinant host cell according to claim 11, wherein the bacterium is a Deinococcus bacterium selected from the group consisting of *D. geothermalis, D. aquatilis, D. gobiensis, D. cellulolysiticus, D. deserti, D. murravi, D. maricopensis* and *D. radiodurans*.

13. A cell extract of a recombinant host cell according to claim 1.

14. A recombinant expression cassette or vector, comprising a nucleic acid sequence encoding a polypeptide comprising:
   an amino acid sequence having at least 95% identity to SEQ ID NO: 1 and exhibiting L-arabinose isomerase activity, or a functional fragment thereof, or
   an amino acid sequence having at least 95% identity to SEQ ID NO: 3 and exhibiting L-ribulokinase activity, or a functional fragment thereof, or
   an amino acid sequence having at least 95% identity to SEQ ID NO: 5 and exhibiting L-ribulase-5-phosphate 4 epimerase activity, or a functional fragment thereof,
   wherein the functional fragment is at least 100 contiguous amino acids of said polvpeptide, and retains the enzymatic activity of the entire polypeptide, and
   wherein the nucleic acid sequence is operably linked to a promoter which is heterologous to said nucleic acid sequence.

15. A recombinant *Deinococcus* bacterium or related bacterium comprising a heterologous nucleic acid sequence encoding a polypeptide exhibiting L-arabinose isomerase activity, a polypeptide exhibiting L-ribulokinase activity, and/or a polypeptide exhibiting L-ribulose-5-phosphate 4 epimerase activity, said bacterium comprising one or several recombinant expression cassettes and/or expression vectors of claim 14, and wherein the related bacterium is selected from the group consisting of *Truepera, Thermus, Meiothertnus, Marinithermus, Oceanithermus, Vulcanithermus, Bacillus, Microbacterium, Cellulosimicrobium, Methylobacteritn, Sphingobacterium, Pseudomonas, Caldimonas, Paenihacillus, Gordonia, Rhodococcus, Stenotrophomonas, Novosphingobium, Sphingomonas, Flavobacterium, Sphingobium, Sphingopyxis, Tepidimonas, Exiguobacterium, Nocardia, Arthrobacter, Kineococcus, Williamsia, Porphyrobacter, Geodermatophylus, Hymenobacter, Kineococcus, Kocuria, Methylobacterium, Halobacterium salinarum, Chroococcidiopsis, Pyrococcus abissis* and *Lactobacillus plantarum* bacteria.

16. The recombinant bacterium of claim 15, wherein the bacterium is a *Deinococcus* bacterium selected from the group consisting of *D. geothermalis, D. cellulolysiticus, D. aquatilis, D. gobiensis, D. deserti, D. murrayi, D. maricopensis* and *D. radiodurans*.

17. A method of producing a polypeptide comprising:
   (a) culturing a host cell according to claim 1 and expressing said polypeptide; and
   (b) recovering said polypeptide from the cell culture; and
   (c) optionally, purifying said polypeptide,
   wherein the polypeptide comprises:
      an amino acid sequence having at least 95% identity to SEQ ID NO: 1 and exhibiting L-arabinose isomerase activity, or a functional fragment thereof, or
      an amino acid sequence having at least 95% identity to SEQ ID NO: 3 and exhibiting L-ribulokinase activity, or a functional fragment thereof, or
      an amino acid sequence having at least 95% identity to SEQ ID NO: 5 and exhibiting L-ribulase-5-phosphate 4 epimerase activity, or a functional fragment thereof,
      and wherein the functional fragment is at least 100 contiguous amino acids of said polypeptide, and retains the enzymatic activity of the entire polypeptide.

18. A method of producing a fermentation product comprising contacting an arabinose containing substrate with a recombinant host cell of claim 1 and optionally recovering the fermentation product.

19. The method according to claim 18, wherein the fermentation product is biofuel, an organic acid, and their salts or esters, an isoprenoid compound, carotenoids, drug or a phaiinaceutical compound.

* * * * *

UNITED STATES PATENT AND TRADEMARK OFFICE
CERTIFICATE OF CORRECTION

PATENT NO. : 10,392,623 B2  
APPLICATION NO. : 15/548424  
DATED : August 27, 2019  
INVENTOR(S) : Rémi Bernard et al.

It is certified that error appears in the above-identified patent and that said Letters Patent is hereby corrected as shown below:

In the Specification

Column 24,  
Line 2, "$NaH_2PO_4.H_2O10$ mM;" should read --$NaH_2PO_4.H_2O$ 10 mM;--.  
Line 40, "$(NH_4)_6Mo7O_{24}.4H_2O$" should read --$(NH_4)_6Mo_7O_{24}.4H_2O$--.

Column 25,  
Line 19, "$CuSO_4.5H_2O10$ nM;" should read --$CuSO_4.5H_2O$ 10 nM;--.

In the Claims

Column 40,  
Line 2, "phaiinaceutical" should read --pharmaceutical--.

Signed and Sealed this  
Sixteenth Day of June, 2020

Andrei Iancu  
*Director of the United States Patent and Trademark Office*

SEQUENCE LISTING

```
<160> NUMBER OF SEQ ID NOS: 8

<210> SEQ ID NO 1
<211> LENGTH: 500
<212> TYPE: PRT
<213> ORGANISM: Deinococcus roseus

<400> SEQUENCE: 1

Met Pro Asn Thr Ala Ser Pro Arg Leu Trp Phe Val Thr Gly Ser Gln
1               5                   10                  15

His Leu Tyr Gly Pro Glu Thr Leu Lys Gln Val Asp Ala Asn Ser Ala
            20                  25                  30

Glu Leu Val Ser Ala Leu Asn Ala Ser Gly Lys Ile Ser Leu Gln Ile
        35                  40                  45

Glu Phe Lys Gly Val Leu Thr Thr Pro Asp Glu Ile Arg Ala Leu Cys
    50                  55                  60

Leu Gln Ala Asn Ser Thr Pro Asp Cys Ala Gly Ile Ile Leu Trp Met
65                  70                  75                  80

His Thr Phe Ser Pro Ser Lys Met Trp Ile Gly Gly Leu Ser Gln Leu
                85                  90                  95

Gln Lys Pro Phe Cys His Leu His Thr Gln Phe Asn Arg Asp Leu Pro
            100                 105                 110

Trp Asp Ser Ile Asp Met Asp Phe Met Asn Leu Asn Gln Ala Ala His
        115                 120                 125

Gly Asp Arg Glu Ala Gly Phe Leu His Thr Arg Met Arg Leu Asp Arg
    130                 135                 140

Lys Val Val Gly His Tyr Ser Asp Pro Glu Val Gln Glu Arg Leu
145                 150                 155                 160

Gly Val Trp Ala Ser Ala Ala His Gly Trp Phe Asp Leu Gln Gly Ala
                165                 170                 175

Lys Phe Cys Arg Phe Gly Asp Asn Met Arg Phe Val Ala Val Thr Glu
            180                 185                 190

Gly Asp Lys Val Ala Ala Glu Met Arg Phe Gly Phe Ser Val Asn Thr
        195                 200                 205

Tyr Gly Val Gly Asp Leu Val Ala Val Val Asp Ala Val Ser Asp Ser
```

```
            210                 215                 220
Asp Ile Asp Ala Leu Val Ala Glu Tyr Asp Asn Leu Tyr Asp Val Ala
225                 230                 235                 240

Pro Glu Leu Gln Lys Gly Gly Glu Arg His Glu Ser Leu Arg Tyr Ser
                245                 250                 255

Ala Arg Leu Glu Leu Gly Ile Glu Lys Phe Leu Val Asp Gly Gly Phe
            260                 265                 270

Lys Gly Phe Thr Thr Thr Phe Glu Asp Leu His Gly Leu Lys Gln Leu
        275                 280                 285

Pro Gly Met Ala Val Gln Arg Leu Met Ala Arg Gly Tyr Gly Phe Ala
290                 295                 300

Gly Glu Gly Asp Trp Lys Thr Ala Val Leu Leu Arg Ala Leu Lys Thr
305                 310                 315                 320

Met Ser Gly Asn Val Ser Thr Ser Phe Met Glu Asp Tyr Thr Tyr His
                325                 330                 335

Leu Glu Pro Gly Lys His Gln Val Leu Gly Ser His Met Leu Glu Val
            340                 345                 350

Cys Pro Thr Ile Ala Glu Asn Lys Pro Lys Val Glu Ile His Pro Leu
        355                 360                 365

Gly Ile Gly Gly Lys Glu Asp Pro Val Arg Leu Val Phe Asn Ser Gln
370                 375                 380

Lys Gly Glu Ala Ile Asn Val Ser Leu Val Asp Leu Gly Ser Arg Phe
385                 390                 395                 400

Arg Leu Ile Val Asn Glu Val Thr Ala Val Glu His Pro Glu Leu Pro
                405                 410                 415

Asn Leu Pro Val Ala Arg Ala Val Trp Glu Cys Lys Pro Asp Phe Lys
            420                 425                 430

Thr Ala Cys Ala Ala Trp Ile His Ala Gly Gly Ala His His Thr Val
        435                 440                 445

Tyr Ser Tyr Val Leu Thr Ser Glu His Leu Glu Asp Phe Ala Ala Ile
450                 455                 460

Ala Gly Val Glu Leu Val Val Ile Asp Gly Asp Thr Lys Leu Arg Asp
465                 470                 475                 480

Leu Lys Gln Asp Leu Lys Phe Ser Asp Leu Tyr Phe Ala Leu Gly Gln
                485                 490                 495

Gly Leu Arg Val
            500

<210> SEQ ID NO 2
<211> LENGTH: 1503
<212> TYPE: DNA
<213> ORGANISM: Deinococcus roseus

<400> SEQUENCE: 2
atgccaaaca ccgcctcccc cagactctgg ttcgtcacgg gctcccagca cctctacggc    60
cctgaaaccc tcaagcaagt ggatgccaat tcagcagaac tggtttctgc tttgaatgcc   120
tctggcaaaa tctccctgca atcgaattt aaagggtgc tgaccacccc agatgagatc     180
cgggctttgt gtctgcaagc caattcaaca ccagactgcg ccggaatcat cctgtggatg   240
cacaccttct cccccagcaa aatgtggatt ggggggcctca gtcagttgca aaaaccgttc   300
tgccacctgc acaccagtt caatcgggat cttccctggg acagcatcga catggatttc    360
atgaacctca accaggccgc ccatggggac cgcgaagcag gtttcttgca cacccgcatg   420
cgtctggacc gcaaagtggt ggtggggcat tacagcgacc cggaagtgca ggaacgtctg   480
```

```
ggcgtgtggg ccagtgcagc acacggctgg tttgatttgc aaggcgcaaa attctgccgg      540
tttggggaca acatgcgctt cgtggccgtg accgaagggg acaaggtggc tgcagagatg      600
cgcttcgggt tctcggtgaa cacctacggg gtgggcgatc tggtggccgt ggtcgatgct      660
gtttcagaca gtgacattga tgctctggtt gcggaatacg acaacctata cgatgtggcc      720
ccagaactgc aaaaaggtgg ggaacgccat gaatccctga ggtactctgc ccgtctggaa      780
ctgggcatcg agaaattcct cgttgatgga ggcttcaagg ggttcaccac cactttttgaa     840 gacctgcatg gtctgaagca actccccgga atggcggtcc agaggctgat ggccagaggg      900
tacgggtttg ctggcgaagg ggactggaaa acagctgtgc ttttgcgtgc cctgaaaacc      960
atgtctggca acgtctcaac ctctttcatg gaggattaca cctaccacct ggaacccgga     1020
aaacaccagg tgctggggtc gcacatgctg gaagtctgcc cgacgattgc agaaaacaaa     1080
ccgaaagtgg aaattcaccc cttaggcatc ggagggaagg aagacccggt gcgtctggtg     1140
ttcaactccc agaagggcga ggccatcaat gtgtctctgg tggacctggg aagccgtttc     1200
cgtttgatcg tcaacgaggt gacggcagtg gagcaccctg agttgcccaa ccttcctgtg     1260
gcgcgtgcag tgtgggaatg caaaccggat ttcaagaccg cctgtgcagc ctggattcat     1320 gcaggggag cgcaccacac ggtgtattct tatgtgctga ccagtgagca cctggaggat      1380
tttgcagcca tcgcaggcgt tgaactggtg gtgattgatg gggacacgaa gctgcgggac     1440
ctgaaacagg acctgaagtt ctcagacctc tactttgccc ttggacaggg cctccgggtc     1500
tag                                                                   1503

<210> SEQ ID NO 3
<211> LENGTH: 563
<212> TYPE: PRT
<213> ORGANISM: Deinococcus roseus

<400> SEQUENCE: 3

Met Ser Asn Pro Pro Glu Leu Tyr Thr Leu Gly Val Asp Tyr Gly Thr
1               5                   10                  15

Glu Ser Gly Arg Ala Val Val Val Arg Val Ser Asp Gly Leu Glu Leu
            20                  25                  30

Ala Ser Ala Val Thr Ser Tyr Pro His Gly Val Ile Asp His His Leu
        35                  40                  45

Pro Thr Gly Glu Val Leu Pro Pro Asp Trp Ala Leu Gln His Pro Asp
    50                  55                  60

Asp Tyr Leu Glu Val Leu Arg Lys Ala Val Pro Gln Ala Val Gln Leu
65                  70                  75                  80

Ser Gly Val Asn Pro Glu His Ile Val Gly Ile Gly Ile Asp Phe Thr
                85                  90                  95

Ala Cys Thr Met Leu Pro Thr Thr Arg Asp Gly Thr Pro Leu Cys Phe
            100                 105                 110

Leu Pro Glu Leu Lys Ala Glu Lys His Ala Phe Val Lys Leu Trp Lys
        115                 120                 125

His His Ala Ala Gln Ser His Ala Asp Arg Ile Asn Ala Val Ala Ala
    130                 135                 140

Arg Met Gly Glu Lys Trp Leu Pro Arg Tyr Gly Phe Lys Ile Ser Ser
145                 150                 155                 160

Glu Trp Phe Phe Ala Lys Ala Leu Gln Ile Leu Glu Glu Ala Pro Glu
                165                 170                 175

Val Tyr Gln Ala Ala Asp Arg Leu Ile Glu Ala Ala Asp Trp Val Val
```

180                 185                 190
        Trp Gln Leu Thr Gly Ala Glu Ser Arg Asn Thr Cys Thr Ala Gly Tyr
                      195                 200                 205

Lys Ala Met Tyr Gln Asp Gly Gln Phe Pro Ser Arg Asp Tyr Phe Ala
            210                 215                 220

Ala Leu Asn Ala Asp Phe Ala Asp Val Val Glu Lys Met Leu Thr
        225                 230                 235                 240

Glu Leu Ser Pro Leu Gly Gly Lys Ala Gly Thr Leu Ser Ala Arg Ala
                        245                 250                 255

Ala Glu Leu Thr Gly Leu Lys Ala Gly Ile Ala Val Ala Val Ala Asn
                        260                 265                 270

Val Asp Ala His Val Ala Val Pro Ala Ala Thr Val Thr Glu Ala Gly
                    275                 280                 285

Gln Met Val Ala Ile Met Gly Thr Ser Thr Cys His Met Leu Leu Gly
                        290                 295                 300

Glu Lys Leu Arg Glu Val Pro Gly Met Cys Gly Val Val Glu Gly Gly
        305                 310                 315                 320

Ile Ile Pro Gly Leu Tyr Gly Tyr Glu Ala Gly Gln Ser Gly Val Gly
                        325                 330                 335

Asp Ile Phe Gly Trp Phe Val Lys His Ala Val Pro Glu Ser Tyr Val
                        340                 345                 350

Gln Gln Ala Ala Ala Glu Asn Val Ser Val His His Ile Met Glu Arg
                    355                 360                 365

Glu Ala Ser Leu Gln Arg Pro Gly Glu His Gly Leu Ile Ala Leu Asp
                    370                 375                 380

Trp Leu Asn Gly Asn Arg Ser Asn Leu Val Asp Ala Asn Leu Ser Gly
        385                 390                 395                 400

Leu Ile Leu Gly Leu Thr Leu His Thr Arg Ala Pro Asp Ile Tyr Arg
                        405                 410                 415

Ala Leu Ile Glu Ala Thr Ala Tyr Gly Thr Arg Ala Ile Ile Glu Asn
                    420                 425                 430

Phe Arg Ala His Gly Val Pro Val Thr Glu Leu Ile Ile Ala Gly Gly
                    435                 440                 445

Leu Lys Lys Asn Lys Met Leu Met Gln Ile Tyr Ser Asp Val Thr Gly
            450                 455                 460

Leu Pro Leu Ser Ile Val Ala Ser Glu Gln Gly Pro Ala Leu Gly Ser
        465                 470                 475                 480

Ala Ile His Ala Ala Val Ala Ala Gly Ile Tyr Pro Asp Ile Arg Ala
                    485                 490                 495

Ala Ala Lys Thr Met Gly Lys Leu Gln Lys Asn Val Tyr Thr Pro Ile
                    500                 505                 510

Pro Gly Asn Val Lys Val Tyr Gln Glu Leu Tyr Gln Glu Tyr Ile Gln
                    515                 520                 525

Leu His Asp His Phe Gly Arg Gly Leu Asn Asn Val Met Lys Arg Leu
                    530                 535                 540

Lys Lys Ile Ala Gln Thr Glu Pro Glu Glu Val Lys His Ala Ala Ala
        545                 550                 555                 560

Thr Pro Ala

<210> SEQ ID NO 4
<211> LENGTH: 1689
<212> TYPE: DNA
<213> ORGANISM: Deinococcus roseus

<400> SEQUENCE: 4

```
atgagcaacc cgcctgagct ctacaccctc ggggtggatt acggcaccga atcgggccgt      60
gctgtggtgg ttcgtgtctc agatggactg gaacttgcct ctgctgtcac ctcttacccg     120
cacggtgtga tcgatcacca tctcccacc ggcgaggttt gcccccaga ctgggcctta      180
cagcaccccg atgactacct cgaagtcctc agaaaggctg ttccacaggc ggtccagctc     240
agcggtgtga acccagaaca cattgtgggc attggcattg atttcaccgc tgcaccatg      300
ctccccacca cccgtgacgg caccccgctc tgtttcctgc ctgagctcaa agccgaaaag     360
cacgctttcg tgaagctctg gaagcaccat gctgcccaga gccacgcaga ccgcatcaac     420
gcagtggcgg ccagaatggg ggagaagtgg ctgcccagat atggattcaa gatcagcagc     480
gaatggttct cgccaaagc cctgcagatc ctggaagaag ccccggaagt gtaccaggcg      540
gcagatcgac tgatcgaagc ggcagactgg gtggtctggc aactcactgg agcagagagt     600
cgcaacacct gcactgcggg ttacaaagcc atgtatcagg atgggcagtt cccttccaga     660
gattactttg ctgccctgaa cgcggatttt gccgatgtgg tcgaagagaa gatgttgact     720
gagctgtctc cactgggggg caaagcagga acccttctg ccagagccgc tgaactcacg      780
ggtctgaaag caggaattgc cgttgccgtt gcgaatgtg atgcccacgt ggcggttcct      840
gcggcaacag tgaccgaggc aggccagatg gtggccatca tgggaacttc cacctgtcac     900
atgctgcttg gagaaaaact cagagaagtt ccaggcatgt gtggggtggt ggaaggtggc     960
atcatccccg gactttacgg ctatgaagcg ggccaatccg gggtcggaga catcttcggc    1020
tggttcgtga acatgcggt gccagaatcc tacgtccagc aagctgctgc cgaaaatgtg    1080
agcgttcacc atattatgga gagggaagcc agcctgcaac gccctgggga cacggattg    1140
attgcgctgg actggttgaa cggcaaccgc agcaacctcg tcgatgccaa tttgagcggt    1200
ctgatccttg gactcacctt gcacacccgt gccccggaca tctaccgggc cctgattgaa    1260
gccacagctt acggaaccag agcgatcatc gagaacttcc gtgcacatgg ggtgcccgtg    1320
accgaactga tcattgccgg agggctgaag aaaaacaaaa tgctgatgca gatttacagc    1380
gatgtcacgg gacttcccct gagcatcgtg gcttcggagc agggtccagc gctgggaagt    1440
gcaattcatg ctgccgtggc tgcaggaatc taccctgaca tccgggcagc agccaaaacc    1500
atggggaaac tgcagaagaa cgtttacacc cccattcccg ggaatgtgaa agtgtatcag    1560
gagctgtatc aggaatacat ccagctgcac gaccattttg gcagagggct caacaacgtg    1620
atgaaacgcc tcaagaaaat cgctcagaca gaacccgaag aggtgaaaca tgctgctgcc    1680
acacctgcg                                                           1689
```

<210> SEQ ID NO 5
<211> LENGTH: 217
<212> TYPE: PRT
<213> ORGANISM: Deinococcus roseus

<400> SEQUENCE: 5

```
Met Leu Leu Pro His Leu Arg Glu Glu Leu Cys Lys Ala His Leu Gln
1               5                   10                  15

Leu Pro Ala Gln Gly Leu Val Thr Trp Thr Ser Gly Asn Ile Ser Val
            20                  25                  30

Leu Asp Glu Arg Glu Gly Leu Met Val Ile Lys Pro Ser Gly Leu Leu
        35                  40                  45

Phe Glu Glu Leu Thr Pro Glu Ser Met Val Val Leu Asp Leu Asp Gly
    50                  55                  60
```

-continued

```
Lys Val Ile Glu Gly Lys Tyr Lys Pro Ser Ser Asp Thr Ala Thr His
 65                  70                  75                  80

Ala Tyr Ile Tyr Arg His Leu Pro His Val Arg Ser Ile Ile His Thr
                 85                  90                  95

His Ser Ala Tyr Ala Thr Ala Trp Ala Ala Asn Asn Arg Glu Ile Pro
            100                 105                 110

Cys Ile Leu Thr Ala Met Ala Asp Glu Phe Gly Gly Pro Ile Pro Cys
        115                 120                 125

Gly Gly Phe Ala Leu Ile Gly Gly Glu Ile Gly Lys Glu Val Val
    130                 135                 140

Lys Thr Leu Ser Gly His Arg Ser Pro Ala Val Ile Leu Lys Asn His
145                 150                 155                 160

Gly Val Phe Thr Ile Gly Glu Ser Ile Gln Lys Ala Leu Lys Ala Ala
                165                 170                 175

Val Met Cys Glu Asp Val Ala Lys Thr Val His Leu Ala Tyr Gln Leu
            180                 185                 190

Gly Thr Pro Glu Lys Leu Asp His Ala Asp Ile Asp Lys Leu Tyr Asp
        195                 200                 205

Arg Tyr Thr His Val Tyr Gly Gln Lys
    210                 215
```

<210> SEQ ID NO 6
<211> LENGTH: 651
<212> TYPE: DNA
<213> ORGANISM: Deinococcus roseus

<400> SEQUENCE: 6

```
atgctgctgc cacacctgcg tgaagaactg tgcaaagcac acctgcaact ccctgcccag    60
ggactcgtca cctggaccag tgggaacatc agcgttctgg acgagaggga aggtctgatg   120
gtcatcaaac cctcgggtct gctctttgaa gaactcaccc ctgaaagcat ggtggtgctg   180
gatctggacg gcaaagtcat cgaagggaag tacaaaccct cttcggacac cgccacccat   240
gcttacatct accgccacct gccccatgtg cgcagcatca tccacaccca cagtgcgtat   300
gccacagctt gggcagccaa caaccggaa attccctgca tcctcaccgc catggccgat   360
gaatttggag gaccgatccc ctgcggtggc tttgccctga ttggcgggga agaaatcggg   420
aaggaagtgg tgaaaaccct ctccgggcac cgttcccctg cggtcatcct caaaaaccac   480
ggggtcttca ccatcggaga atccatccag aaagccctga agccgccgt gatgtgtgaa   540
gacgtggcaa aaacggtgca tctggcgtac cagctgggga caccagagaa gcttgatcat   600
gcagacatcg acaaactcta cgaccggtac acgcacgtgt acggacagaa a            651
```

<210> SEQ ID NO 7
<211> LENGTH: 23
<212> TYPE: DNA
<213> ORGANISM: Artificial Sequence
<220> FEATURE:
<223> OTHER INFORMATION: Forward primer to amplify 16S rDNA

<400> SEQUENCE: 7

```
gttacccgga atcactgggc gta                                             23
```

<210> SEQ ID NO 8
<211> LENGTH: 23
<212> TYPE: DNA
<213> ORGANISM: Artificial Sequence
<220> FEATURE:

```
<223> OTHER INFORMATION: Reverse primer to amplify 16S rDNA

<400> SEQUENCE: 8
ggtatctacg cattccaccg cta                                         23
```